(12) United States Patent
Brooks et al.

(10) Patent No.: US 11,826,405 B2
(45) Date of Patent: Nov. 28, 2023

(54) NEUROTOXIN COMPOSITIONS FOR USE IN TREATING HEADACHE

(71) Applicant: AEON Biopharma, Inc., Newport Beach, CA (US)

(72) Inventors: Gregory F. Brooks, Irvine, CA (US); Andrew M. Blumenfeld, Del Mar, CA (US)

(73) Assignee: Aeon Biopharma, Inc., Irvine, CA (US)

( * ) Notice: Subject to any disclaimer, the term of this patent is extended or adjusted under 35 U.S.C. 154(b) by 309 days.

(21) Appl. No.: 17/006,685

(22) Filed: Aug. 28, 2020

(65) Prior Publication Data

US 2021/0060144 A1    Mar. 4, 2021

Related U.S. Application Data

(60) Provisional application No. 63/029,304, filed on May 22, 2020, provisional application No. 63/011,168, filed on Apr. 16, 2020, provisional application No. 62/950,775, filed on Dec. 19, 2019, provisional application No. 62/894,540, filed on Aug. 30, 2019.

(51) Int. Cl.
*A61K 38/48* (2006.01)
*A61P 25/06* (2006.01)
*A61P 25/16* (2006.01)

(52) U.S. Cl.
CPC .......... *A61K 38/4893* (2013.01); *A61P 25/16* (2018.01); *C12Y 304/24069* (2013.01)

(58) Field of Classification Search
None
See application file for complete search history.

(56) References Cited

U.S. PATENT DOCUMENTS

| 5,714,468 | A | 2/1998 | Binder |
| 7,749,515 | B2 * | 7/2010 | Blumenfeld ............ A61P 25/06 514/17.7 |
| 7,780,968 | B2 | 8/2010 | Donovan |
| 8,420,106 | B1 | 4/2013 | Binder |
| 8,940,308 | B2 | 1/2015 | Turkel et al. |
| 10,111,938 | B2 | 10/2018 | Blumenfeld et al. |
| 10,729,751 | B2 | 8/2020 | Blumenfeld et al. |
| 2010/0114191 | A1 | 5/2010 | Newman |
| 2010/0266638 | A1 | 10/2010 | Turkel et al. |
| 2020/0360492 | A1 | 11/2020 | Blumenfeld et al. |

FOREIGN PATENT DOCUMENTS

| WO | 2019/005773 A1 | 1/2019 |
| WO | 2021/041978 A1 | 3/2021 |

OTHER PUBLICATIONS

McAllister, "Improvement of headache symptoms and reduction in headache medication usage in patients treated with botulinum toxin type A", Journal of Medical Economics, vol. 7, pp. 19-28. (Year: 2004).*
Popoff et al., "Clostridial toxins", Future Microbiology, vol. 4(8), p. 1021-1064. (Year: 2009).*
International Search Report and Written Opinion, dated Dec. 3, 2020, for International Application Serial No. PCT/US2020/048624 filed Aug. 28, 2020, 16 pages.

* cited by examiner

*Primary Examiner* — Michelle F. Paguio Frising
*Assistant Examiner* — Grant C Currens
(74) *Attorney, Agent, or Firm* — K&L Gates LLP; Louis C. Cullman; Hal Gibson

(57) ABSTRACT

Disclosed herein are compositions and methods for use in treating headache.

30 Claims, 8 Drawing Sheets

NEUROTOXIN COMPOSITIONS FOR USE IN TREATING HEADACHE

CROSS-REFERENCE TO RELATED APPLICATIONS

This application claims the benefit of the filing date of U.S. Appl. No. 62/894,540, filed Aug. 30, 2019, U.S. Appl. No. 62/950,775, filed Dec. 19, 2019, U.S. Appl. No. 63/011,168, filed Apr. 16, 2020, and U.S. Appl. No. 63/029,304, filed May 22, 2020, each of which is incorporated herein by reference in its entirety.

FIELD

The present specification relates the use of neurotoxins to treat headaches, for example migraine headaches.

BACKGROUND

Migraine is a disabling headache disorder affecting millions in the general adult population, and considered the most common type of primary chronic daily headache in the United States. In the Global Burden of Disease Study by the World Health Organization, updated in 2013, migraine was found to be the sixth-highest cause worldwide of years lost due to disability. Migraine attacks can increase in frequency over time. Experts divide this process of transition into four distinct states:
  No migraine
  Low-frequency episodic migraine (EM) (fewer than 10 headache days per month)
  High-frequency episodic migraine (10-14 headache days per month)
  Chronic migraine (CM) (15 or more headache days per month; meaning that people with chronic migraine have a migraine or headache more often than not).

Per the International Headache Society, CM is defined as headache occurring on 15 or more days per month for more than three months, which, on at least 8 days per month, has the features of migraine headache. CM occurs in approximately 1% of the population. Studies estimate that about 2.5% of people with episodic migraine will transition to chronic migraine each year. CM is linked with suffering, disability, and medication overuse. Only one third of CM patients use headache prophylactic medication.

Currently, Onabotulinumtoxin A (BOTOX®) is the only FDA-approved botulinum toxin preventive treatment for CM. However, this treatment involves numerous injections (over thirty) and a relatively large dosage of the neurotoxin (over 150 Units) per treatment session. Such large doses can, over time, cause a patient to develop an immune reaction to the neurotoxin, as the immune response is often triggered by larger doses and/or injection volumes. In addition, certain patients experience side effects including muscle weakness, for example ptosis (eyelid droop) or neck muscle weakness, as a result of the FDA-approved treatment method. Thus, improved methods could benefit patients.

SUMMARY

Disclosed herein are compositions and methods comprising neurotoxins, for example clostridial neurotoxins, including botulinum toxins, and the use thereof to treat headache, for example migraine, for example EM or CM, with reduced side effects and comparable or improved efficacy as compared to known methods. Disclosed methods comprise the use of both intra-muscular injections and saturation of nerve-rich trigeminal administration sites, for example combining injections into at least one, two, three, four, five, or six areas including the corrugator, procerus, masseter, occipitalis, temporalis, trapezius. Further embodiments can comprise injecting one of but not both of the frontalis and cervical paraspinal muscle regions. Further embodiments can comprise avoiding injecting at least one of or both of the frontalis and cervical paraspinal muscle regions. Disclosed methods comprise the use of both intra-muscular injections and saturation of nerve-rich trigeminal administration sites in combination, for example combining injections into at least one, two, three, four, five, or six areas including the corrugator, procerus, masseter, occipitalis, temporalis, and trapezius. Further embodiments can comprise injecting one of but not both of the frontalis and cervical paraspinal muscle regions. Further embodiments can comprise avoiding injecting at least one of or both of the frontalis and cervical paraspinal muscle regions, combined with injection into the sphenopalatine ganglion (SPG).

Further disclosed embodiments comprise the use of both intra-muscular injections and saturation of nerve-rich trigeminal administration sites, for example combining injections into at least one, two, three, four, five, six, seven, or eight areas including the nasalis, orbicularis oculi, corrugator, procerus, masseter, occipitalis, temporalis, and trapezius muscle regions. Further embodiments can comprise injecting one of but not both of the frontalis and cervical paraspinal muscle regions. Further embodiments can comprise avoiding injecting at least one of or both of the frontalis and cervical paraspinal muscle regions. Disclosed methods comprise the use of both intra-muscular injections and saturation of nerve-rich trigeminal administration sites in combination, for example combining injections into at least one, two, three, four, five, six, seven, or eight areas including the nasalis, orbicularis oculi, corrugator, procerus, masseter, occipitalis, temporalis, and trapezius muscle regions with injection into the sphenopalatine ganglion (SPG). Further embodiments can comprise injecting one of but not both of the frontalis and cervical paraspinal muscle regions. Further embodiments can comprise avoiding injecting at least one of or both of the frontalis and cervical paraspinal muscle regions.

Disclosed methods comprise the use of both intra-muscular injections and saturation of nerve-rich trigeminal administration sites in combination, for example combining injections into at least one, two, three, four, five, or six areas including the corrugator, procerus, masseter, occipitalis, temporalis, and trapezius muscle regions with a follow-up injection after an evaluation period into the sphenopalatine ganglion (SPG) or into the pterygopalatine space to block the SPG, for example if additional dosing is needed to enhance the efficacy. In embodiments, the evaluation period can be, for example, 4 weeks, 5 weeks, 6 weeks, 7 weeks, 8 weeks, 9 weeks, 10 weeks, 11 weeks, 12 weeks, 14 weeks, or more. Further embodiments can comprise injecting one of but not both of the frontalis and cervical paraspinal muscle regions. Further embodiments can comprise avoiding injecting at least one of or both of the frontalis and cervical paraspinal muscle regions.

Disclosed methods comprise the use of both intra-muscular injections and saturation of nerve-rich trigeminal administration sites in combination, for example combining injections into at least one, two, three, four, five, six, seven, or eight areas including the nasalis, orbicularis oculi, corrugator, procerus, masseter, occipitalis, temporalis, and trapezius muscle regions with a follow-up injection after an evaluation period into the sphenopalatine ganglion (SPG) or into the pterygopalatine space to block the SPG, if additional dosing is needed to enhance the efficacy. In embodiments, the evaluation period can be, for example, 4 weeks, 5 weeks, 6 weeks, 7 weeks, 8 weeks, 9 weeks, 10 weeks, 11 weeks, 12 weeks, 14 weeks, or more. Further embodiments can comprise injecting one of but not both of the frontalis and cervical paraspinal muscle regions. Further embodiments can comprise avoiding injecting at least one of or both of the frontalis and cervical paraspinal muscle regions.

Disclosed methods comprise the use of both intra-muscular injections and saturation of nerve-rich trigeminal administration sites in combination, for example combining injections into at least one, two, three, four, five, six, seven, or eight areas including the nasalis, orbicularis oculi, corrugator, procerus, masseter, occipitalis, temporalis, and trapezius muscle regions with a follow-up injection after an evaluation period into the sphenopalatine ganglion (SPG) or into the pterygopalatine space to block the SPG, if additional dosing is needed to enhance the efficacy, combined with injections into at least one, two, three, four, five, six, seven, or eight areas including the nasalis, orbicularis oculi, corrugator, procerus, masseter, occipitalis, temporalis, and trapezius and muscle regions. In embodiments, the evaluation period can be, for example, 4 weeks, 5 weeks, 6 weeks, 7 weeks, 8 weeks, 9 weeks, 10 weeks, 11 weeks, 12 weeks, 14 weeks, or more. Further embodiments can comprise injecting one of but not both of the frontalis and cervical paraspinal muscle regions. Further embodiments can comprise avoiding injecting at least one of or both of the frontalis and cervical paraspinal muscle regions.

Disclosed embodiments comprise the avoidance of treatment to specific areas. By avoiding administration to certain areas, the occurrence and/or severity of side effects can be reduced.

In embodiments, the frontalis is not injected. In embodiments, this avoidance of injection to the frontalis prevents the development of ptosis in the patient.

In embodiments, the cervical paraspinal muscles are not injected. In embodiments, this avoidance of injection to the cervical paraspinal muscles prevents the development of neck weakness in the patient.

In embodiments, the corrugator is not injected.
In embodiments, the masseter is not injected
In embodiments, the procerus is not injected.
In embodiments, the occipitalis is not injected.
In embodiments, the temporalis is not injected.
In embodiments, the trapezius is not injected.
In embodiments, the nasalis is not injected.
In embodiments, the orbicularis oculi is not injected.

Disclosed treatment modalities can prevent or alleviate symptoms of CM, as well as both lessen the total neurotoxin dose administered to a patient and the number of administrations required. Longer duration of effect can also be provided by the disclosed methods. Disclosed combination treatments can provide a synergistic effect. Disclosed methods comprise treatment of migraine with fewer side effects.

As compared to the FDA-approved Onabotulinumtoxin A treatment for chronic migraine, which includes 31 injections into all 7 of the following muscle regions: frontalis, corrugator, procerus, occipitalis, temporalis, trapezius, and cervical paraspinal muscle regions, disclosed methods can reduce treatment side effects, including muscle weakness, for example ptosis, neck weakness, and the like. For example, disclosed methods comprise avoiding administration, for example injection, into the frontalis muscle, thus reducing the risk of ptosis. Further embodiments comprise avoiding administration, for example injection, into the cervical paraspinal muscles, thus reducing the risk of neck weakness.

Disclosed methods comprise fixed-site, fixed-dose methods targeting both sensory and motor effects. Disclosed methods provide for fewer injection sites as compared to current practices, as well as specialized treatments for EM and CM.

Embodiments comprise injection of the nasalis for patients experiencing nasal, facial or orbital pain or sensitivity associated with migraines or headaches.

Embodiments comprise injection of the masseter for patients experiencing masseter muscle pain or tightness or masseter hypertrophy (bulging masseter) or teeth clenching associated with migraines or headaches.

In embodiments, the corrugator muscle is injected parallel to the muscle.

Disclosed embodiments include injection techniques that can minimize adverse effects, for example bruising, for example bruising associated with oculi injection. Disclosed embodiments include injection techniques comprising "injection threading," an injection technique whereby the needle is inserted in a parallel, diagonal, or longitudinal direction into the muscle and toxin is gradually released as the needle is withdrawn. Disclosed embodiments can eliminate injection to the procerus, for example by utilizing a corrugator injection technique comprising injection into the corrugator parallel to the corrugator muscle utilizing injection threading to cover the procerus region.

DETAILED DESCRIPTION

Figure 1:
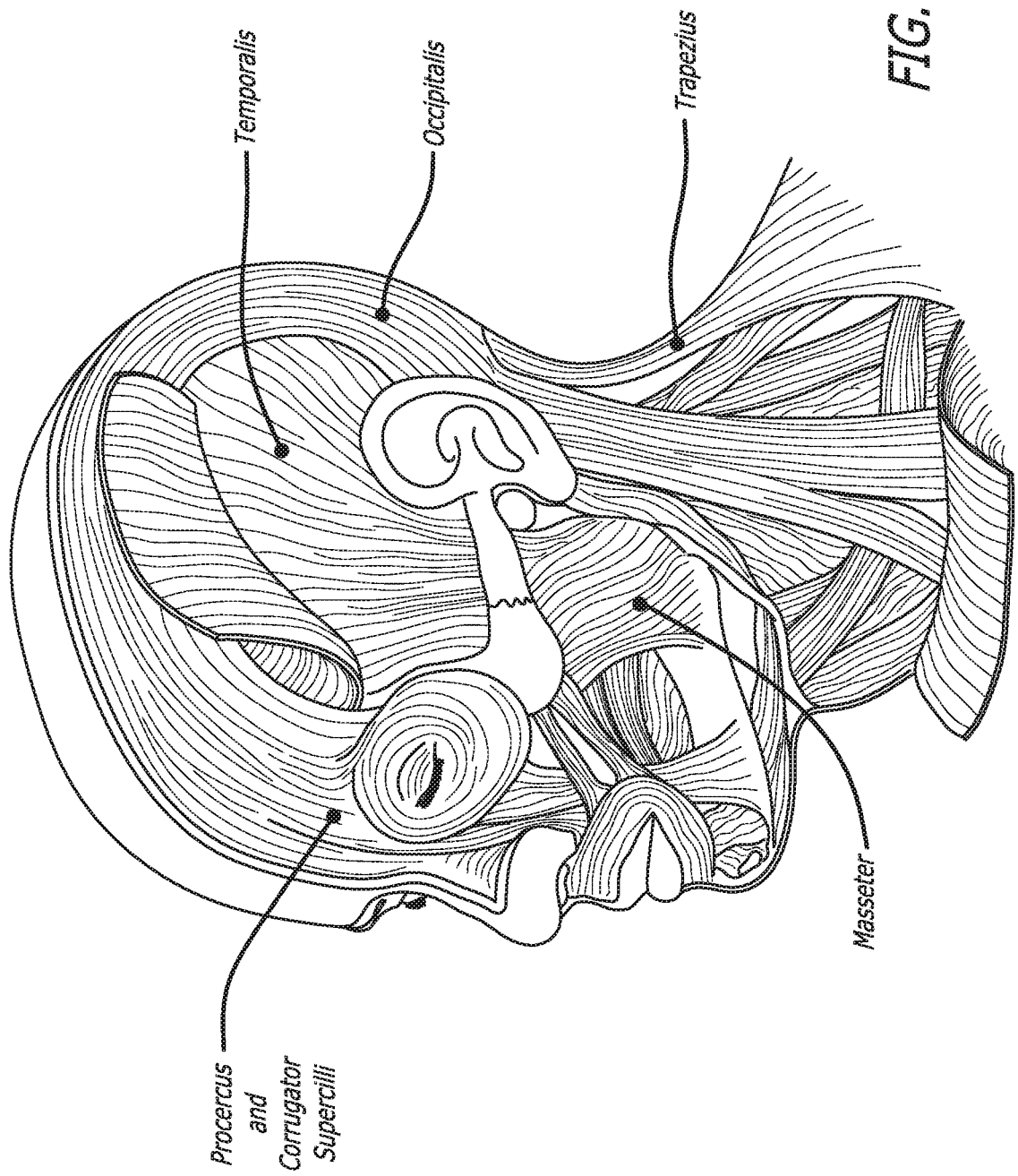
FIG. 1 shows the approximate location of several injection sites in various muscle regions disclosed herein.
Figure 2:
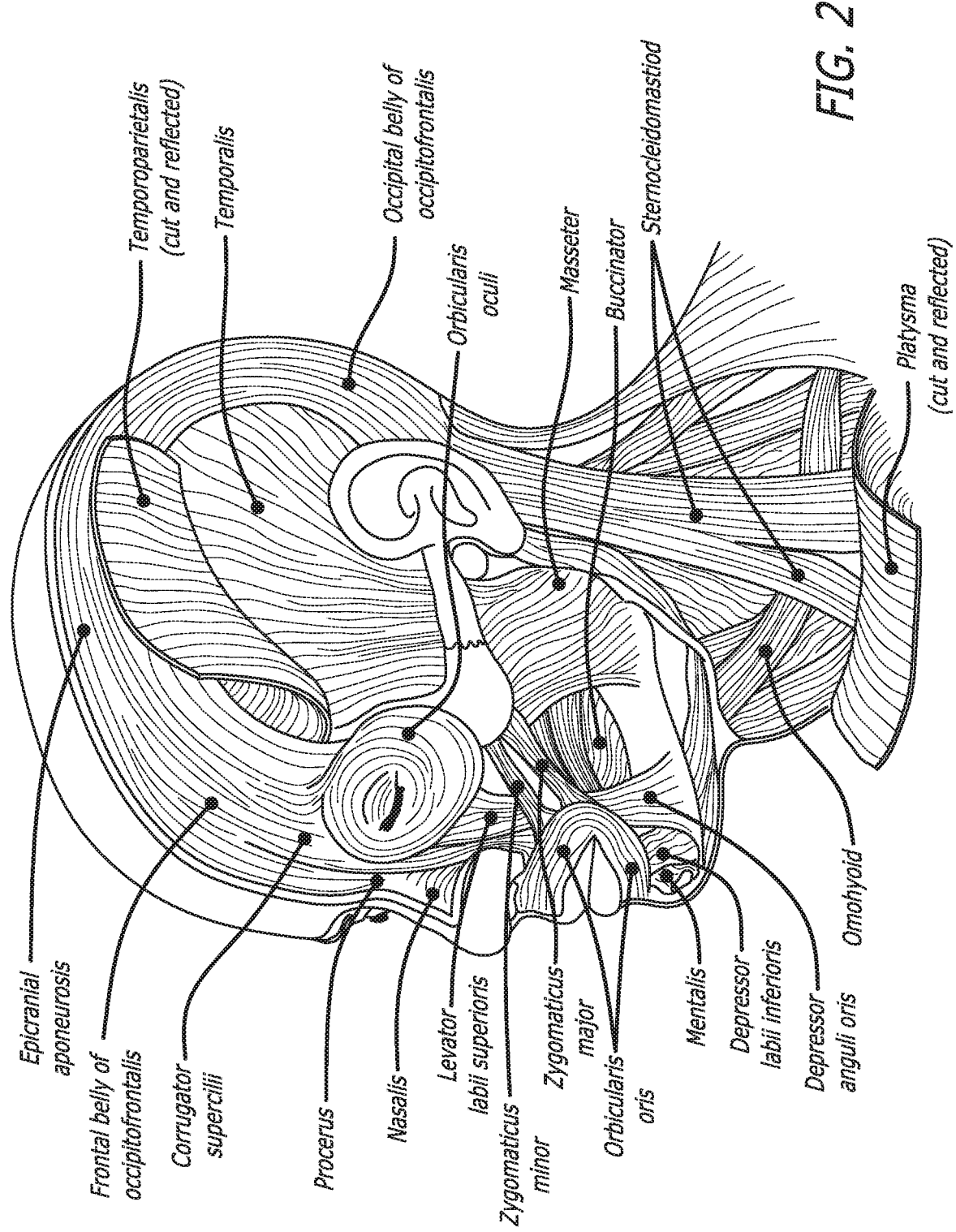
FIG. 2 shows the approximate location of several injection sites in various muscle regions disclosed herein.
Figure 3:
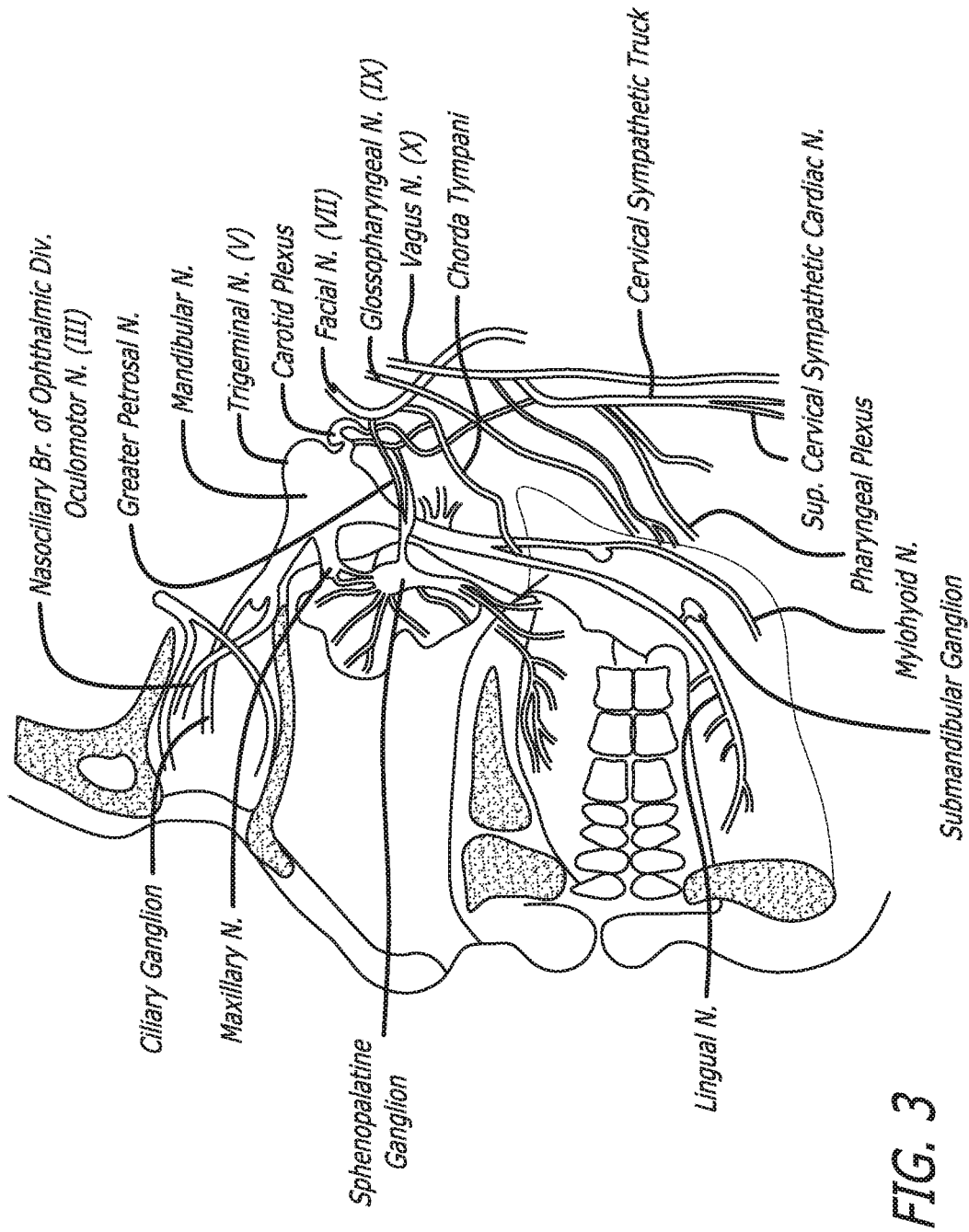
FIG. 3 shows the Sphenopalatine Ganglion.

The present disclosure is directed toward methods for reducing the occurrence and alleviating the severity of side effects associated with neurotoxin treatment of headaches in migraine patients, for example CM or EM patients.

The trigeminal nerve is involved with pain sensations resulting from a number of headache types, including headaches triggered by other pathologies. The sphenopalatine ganglion (SPG), largest of the sympathetic ganglion associated with the branches of the trigeminal nerve, is deeply placed in the pterygopalatine fossa, close to the sphenopalatine foramen. It is triangular or heart shaped, of a reddish-gray color, and is situated just below the maxillary nerve as it crosses the fossa. It receives a sensory, a motor and a sympathetic root. The sensory root is derived from two sphenopalatine branches of the maxillary nerve; their fibers, for the most part, pass directly into the palatine nerves. A few of the fibers, however, enter the ganglion, constituting its sensory root.

Disclosed embodiments can comprise administering a therapeutically effective amount of at least one neurotoxin bi-laterally into the SPG. In embodiments comprising injection into the SPG, suitable compositions can comprise clostridial neurotoxins, for example botulinum neurotoxins. The administration can comprise injection(s), for example through the cheek, intra-oral injection, or intra-nasal injection.

Disclosed embodiments further comprise administering a therapeutically effective amount of at least one neurotoxin to a nerve associated with at least one of the nasalis, orbicularis oculi, corrugator, procerus, masseter, occipitalis, temporalis, and trapezius muscle regions. In embodiments comprising injection into at least one of the nasalis, orbicularis oculi, corrugator, procerus, masseter, occipitalis, temporalis, and trapezius muscle regions, suitable compositions can comprise clostridial neurotoxins, for example botulinum neurotoxins. Further embodiments can comprise injecting one of but not both of the frontalis and cervical paraspinal muscle regions. Further embodiments can comprise avoiding injecting at least one of or both of the frontalis and cervical paraspinal muscle regions.

Embodiments comprise lower-dose neurotoxin administrations as compared to methods known in the art. For example, the patient's sensitivity to and tolerance of the neurotoxin can be determined in the initial treatment by administering a low dosage (in embodiments, 50-100 Units) at one or more primary trigeminal target sites previously described along the trigeminal nerve including selection of the frontalis, corrugator, procerus, masseter, occipitalis, temporalis, trapezius and cervical paraspinal muscle regions along with the additional targeted administrations of a low dose of neurotoxin (in embodiments, 25-50 Units) delivered bilaterally, intra-orally, intra-nasally, or through the cheek into the SPG if additional dosing is needed after, for example, 4 weeks, 5 weeks, 6 weeks, 8 weeks, 10 weeks, twelve weeks, 14 weeks, 16 weeks, or the like.

In embodiments, the amount of neurotoxin administered into the SPG is, for example half the amount administered into the trigeminal target sites. In embodiments, the amount of neurotoxin administered into the SPG is less than half the amount administered into the trigeminal target sites. In embodiments, the amount of neurotoxin administered into the SPG is one-third the amount administered into the trigeminal target sites, or less.

Embodiments comprise fewer neurotoxin administrations as compared to methods known in the art. For example, in contrast to current FDA-approved botulinum CM treatments which utilize 31 injections into 7 head and neck muscle areas, disclosed embodiments comprise at least 2 injections into the SPG and up to 15 injections into at least one, two, three, four, five, six, seven, or eight of the nasalis, orbicularis oculi, corrugator, procerus, masseter, occipitalis, temporalis, and trapezius muscle regions. Further embodiments can comprise injecting one of but not both of the frontalis and cervical paraspinal muscle regions. Further embodiments can comprise avoiding injecting at least one of or both of the frontalis and cervical paraspinal muscle regions. Further, by avoiding administration into certain areas, for example the frontalis and/or the cervical paraspinal muscles, side effects such as eyelid droop and muscle weakness can be decreased.

Definitions

"Administration," or "to administer" means the step of giving (i.e. administering) a pharmaceutical composition or active ingredient to a subject. The pharmaceutical compositions disclosed herein can be administered via a number of appropriate routes, including oral, intramuscular, subdermal or subcutaneous routes of administration, such as by injection or use of an implant. Intramuscular injections can be, for example, superficial or intermediate.

"Botulinum toxin" or "botulinum neurotoxin" means a neurotoxin derived from *Clostridium botulinum*, as well as modified, recombinant, hybrid and chimeric botulinum toxins. A recombinant botulinum toxin can have the light chain and/or the heavy chain thereof made recombinantly by a non-clostridial species. "Botulinum toxin," as used herein, encompasses the botulinum toxin serotypes A, B, C, D, E, F, G and H. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the disclosed embodiments.

"Clostridial neurotoxin" means a neurotoxin produced from, or native to, a clostridial bacterium, such as *Clostridium botulinum*, *Clostridium butyricum* or *Clostridium beratti*, as well as a Clostridial neurotoxin made recombinantly by a non-Clostridial species.

"Fast-acting" as used herein refers to a botulinum toxin that produces effects in the patient more rapidly than those produced by, for example, a botulinum neurotoxin type A. For example, the effects of a fast-acting botulinum toxin (such as botulinum type E) can be produced within 36 hours.

"Fast-recovery" as used herein refers to a botulinum toxin that whose effects diminish in the patient more rapidly than those produced by, for example, a botulinum neurotoxin type A. For example, the effects of a fast-recovery botulinum toxin (such as botulinum type E) can diminish within, for example, 120 hours, 150 hours, 300 hours, 350 hours, 400 hours, 500 hours, 600 hours, 700 hours, 800 hours, or the like. It is known that botulinum toxin type A can have an efficacy for up to 12 months, and in some circumstances for as long as 27 months, when used to treat glands, such as in the treatment of hyperhidrosis. However, the usual duration of an intramuscular injection of a botulinum neurotoxin type A is typically about 3 to 4 months.

"Neurotoxin" means a biologically active molecule with a specific affinity for a neuronal cell surface receptor. Neurotoxin includes clostridial toxins both as pure toxin and as complexed with one to more non-toxin, toxin-associated proteins.

"Patient" means a human or non-human subject receiving medical or veterinary care.

"Pharmaceutical composition" means a formulation in which an active ingredient can be a clostridial toxin. The word "formulation" means that there is at least one additional ingredient (such as, for example and not limited to, an albumin [such as a human serum albumin or a recombinant human albumin] and/or sodium chloride) in the pharmaceutical composition in addition to a botulinum neurotoxin active ingredient. A pharmaceutical composition is therefore a formulation which is suitable for diagnostic, therapeutic or cosmetic administration to a subject, such as a human patient. The pharmaceutical composition can be: in a lyophilized or vacuum dried condition, a solution formed after reconstitution of the lyophilized or vacuum dried pharmaceutical composition with saline or water, for example, or; as a solution that does not require reconstitution. As stated, a pharmaceutical composition can be liquid, semi-solid, or solid. A pharmaceutical composition can be animal-protein free.

"Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 95%, and more preferably at least 99% of the non-botulinum toxin proteins and impurities removed.

"Therapeutic formulation" means a formulation that can be used to treat and thereby alleviate a disorder or a disease and/or symptom associated thereof.

"Therapeutically effective amount" means the level, amount or concentration of an agent (e.g. such as a clostridial toxin or pharmaceutical composition comprising clostridial toxin) needed to treat a disease, disorder or condition without causing significant negative or adverse side effects.

"Treat," "treating," or "treatment" means an alleviation or a reduction (which includes some reduction, a significant reduction a near total reduction, and a total reduction), resolution or prevention (temporarily or permanently) of a symptom, disease, disorder or condition, so as to achieve a desired therapeutic or cosmetic result, such as by healing of injured or damaged tissue, or by altering, changing, enhancing, improving, ameliorating and/or beautifying an existing or perceived symptom, disease, disorder or condition.

"Unit" or "U" means an amount of active botulinum neurotoxin standardized to have equivalent neuromuscular blocking effect as a Unit of commercially available botulinum neurotoxin type A (for example, Onabotulinumtoxin A (BOTOX®)).

Neurotoxin Compositions

Embodiments disclosed herein comprise neurotoxin compositions. Such neurotoxins can be formulated in any pharmaceutically acceptable formulation in any pharmaceutically acceptable form. The neurotoxin can also be used in any pharmaceutically acceptable form supplied by any manufacturer. Disclosed embodiments comprise use of clostridial neurotoxins.

The clostridial neurotoxin can be made by a clostridial bacterium, such as by a *Clostridium botulinum, Clostridium butyricum*, or *Clostridium beratti* bacterium. Additionally, the neurotoxin can be a modified neurotoxin; that is a neurotoxin that has at least one of its amino acids deleted, modified or replaced, as compared to the native or wild type neurotoxin. Furthermore, the neurotoxin can be a recombinantly produced neurotoxin or a derivative or fragment thereof.

In disclosed embodiments, the neurotoxin is formulated in unit dosage form; for example, it can be provided as a sterile solution in a vial or as a vial or sachet containing a lyophilized powder for reconstituting in a suitable vehicle such as saline for injection.

In embodiments, the botulinum toxin is formulated in a solution containing saline and pasteurized Human Serum Albumin (HSA), which stabilizes the toxin and minimizes loss through non-specific adsorption. The solution can be sterile filtered (0.2 µm filter), filled into individual vials, and then vacuum-dried to give a sterile lyophilized powder. In use, the powder can be reconstituted by the addition of sterile unpreserved normal saline (sodium chloride 0.9% for injection).

In an embodiment, botulinum type A is supplied in a sterile solution for injection with a 5-mL vial nominal concentration of 20 ng/mL in 0.03 M sodium phosphate, 0.12 M sodium chloride, and 1 mg/mL HSA, at pH 6.0.

Although the composition may only contain a single type of neurotoxin, for example botulinum type A, disclosed compositions can include two or more types of neurotoxins, which can provide enhanced therapeutic effects of the disorders. For example, a composition administered to a patient can include botulinum types A and E. Administering a single composition containing two different neurotoxins can permit the effective concentration of each of the neurotoxins to be lower than if a single neurotoxin is administered to the patient while still achieving the desired therapeutic effects. This type of "combination" composition can also provide benefits of both neurotoxins, for example, quicker effect combined with longer duration.

The composition administered to the patient can also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors.

Disclosed fast-acting neurotoxin compositions can be injected into the patient using a needle or a needleless device. In certain embodiments, the method comprises injecting the composition sub-dermally, subcutaneously, intramuscularly, or through superficial intramuscular injections, into the individual. For example, administering may comprise injecting the composition through a 27 gauge needle, 28 gauge needle, 29 gauge needle, 30 gauge needle, 31 gauge needle, 32 gauge needle, and/or a 33 gauge needle. In certain embodiments, the method comprises administering a composition comprising a botulinum toxin type A.

Administration of the disclosed compositions can be carried out by any suitable means, for example by syringe, catheters, needles and other means for injecting. The injection can be performed on any area of the mammal's body that is in need of treatment, however disclosed embodiments contemplate injection into the patient's head (for example, nerve and muscle locations indicated in FIGS. 1-8). The injection can be into any specific area such as epidermis, dermis, fat, muscle, nerve junction, or subcutaneous layer. Disclosed embodiments can comprise avoiding injecting certain areas, for example avoiding injecting at least one of or both of the frontalis and cervical paraspinal muscle regions.

More than one injection and/or sites of injection may be necessary to achieve the desired result. Also, some injections, depending on the location to be injected, may require the use of fine, hollow, Teflon®-coated needles, in certain embodiments guided, for example by electromyography.

The frequency and the amount of injection under the disclosed methods can be determined based on the nature and location of the particular area being treated. In certain cases, however, repeated injection may be desired to achieve optimal results. The frequency and the amount of the injection for each particular case can be determined by the person of ordinary skill in the art.

Although examples of routes of administration and dosages are provided, the appropriate route of administration and dosage are generally determined on a case by case basis by the attending physician. For example, the route and dosage for administration of a clostridial neurotoxin according to the present disclosed invention can be selected based upon criteria such as the solubility characteristics of the neurotoxin chosen as well as the intensity and scope of the condition being treated.

Methods of Use

Methods disclosed herein can comprise administration of a neurotoxin, for example a clostridial toxin, for example a botulinum type A, to a patient with CM to prevent or alleviate the symptoms associated with CM. For example, disclosed methods can prevent or alleviate the occurrence of pain, nausea, vomiting, light sensitivity, sound sensitivity, and combinations thereof.

In embodiments, methods comprise administering a therapeutically effective amount of at least one neurotoxin to a nerve associated with at least one of the nasalis, orbicularis oculi, corrugator, procerus, masseter, occipitalis, temporalis, and trapezius muscle regions. Further embodiments comprise the avoidance of injections to specific muscles. For example, disclosed methods comprise avoiding administration, for example injection, into the frontalis muscle, thus reducing the risk of ptosis. Further embodiments comprise avoiding administration, for example injection, into the cervical paraspinal muscles, thus reducing the risk of neck weakness.

In embodiments, methods comprise administering a therapeutically effective amount of at least one neurotoxin to a nerve associated with at least two of the nasalis, orbicularis oculi, corrugator, procerus, masseter, occipitalis, temporalis, and trapezius muscle regions. In embodiments, methods comprise administering a therapeutically effective amount of at least one neurotoxin to a nerve associated with at least three of the nasalis, orbicularis oculi, corrugator, procerus, masseter, occipitalis, temporalis, and trapezius muscle regions. In embodiments, methods comprise administering a therapeutically effective amount of at least one neurotoxin to a nerve associated with at least four of the nasalis, orbicularis oculi, corrugator, procerus, masseter occipitalis, temporalis, and trapezius muscle regions. In embodiments, methods comprise administering a therapeutically effective amount of at least one neurotoxin to a nerve associated with at least five of the nasalis, orbicularis oculi, corrugator, procerus, masseter, occipitalis, temporalis, and trapezius muscle regions. In embodiments, methods comprise administering a therapeutically effective amount of at least one neurotoxin to a nerve associated with at least six of the nasalis, orbicularis oculi, corrugator, procerus, masseter, occipitalis, temporalis, and trapezius muscle regions. In embodiments, methods comprise administering a therapeutically effective amount of at least one neurotoxin to a nerve associated with at least seven of the nasalis, orbicularis oculi, corrugator, procerus, masseter, occipitalis, temporalis, and trapezius muscle regions. In embodiments, methods comprise administering a therapeutically effective amount of at least one neurotoxin to a nerve associated with at least eight of the nasalis, orbicularis oculi, corrugator, procerus, masseter, occipitalis, temporalis, and trapezius muscle regions. In embodiments, methods comprise administering a therapeutically effective amount of at least one neurotoxin to a nerve associated with the nasalis, orbicularis oculi, corrugator, procerus, masseter, occipitalis, temporalis, and trapezius muscle regions. Further embodiments can comprise injecting one of but not both of the frontalis and cervical paraspinal muscle regions. Further embodiments can comprise avoiding injecting at least one of or both of the frontalis and cervical paraspinal muscle regions.

In embodiments, methods comprise avoiding the administration of a therapeutically effective amount of at least one neurotoxin to at least one of the nasalis, orbicularis oculi, frontalis, corrugator, procerus, masseter, occipitalis, temporalis, trapezius and cervical paraspinal muscle regions. By avoiding certain administration locations, side effects can be lessened or eliminated.

In embodiments, methods comprise avoiding the administration of a therapeutically effective amount of at least one neurotoxin to a nerve associated with at least two of the nasalis, orbicularis oculi, frontalis, corrugator, procerus, masseter, occipitalis, temporalis, trapezius and cervical paraspinal muscle regions. By avoiding certain administration locations, side effects can be lessened or eliminated.

In embodiments, methods comprise avoiding the administration of a therapeutically effective amount of at least one neurotoxin to a nerve associated with at least three of the nasalis, orbicularis oculi, frontalis, corrugator, procerus, masseter, occipitalis, temporalis, trapezius and cervical paraspinal muscle regions. By avoiding certain administration locations, side effects can be lessened or eliminated.

In embodiments, methods comprise avoiding the administration of a therapeutically effective amount of at least one neurotoxin to a nerve associated with at least four of the nasalis, orbicularis oculi, frontalis, corrugator, procerus, masseter occipitalis, temporalis, trapezius and cervical paraspinal muscle regions. By avoiding certain administration locations, side effects can be lessened or eliminated.

In embodiments, methods comprise avoiding the administration of a therapeutically effective amount of at least one neurotoxin to a nerve associated with at least five of the nasalis, orbicularis oculi, frontalis, corrugator, procerus, masseter, occipitalis, temporalis, trapezius and cervical paraspinal muscle regions. By avoiding certain administration locations, side effects can be lessened or eliminated.

In embodiments, methods comprise avoiding the administration of a therapeutically effective amount of at least one neurotoxin to a nerve associated with at least six of the nasalis, orbicularis oculi, frontalis, corrugator, procerus, masseter, occipitalis, temporalis, trapezius and cervical paraspinal muscle regions. By avoiding certain administration locations, side effects can be lessened or eliminated.

In embodiments, methods comprise avoiding the administration of a therapeutically effective amount of at least one neurotoxin to a nerve associated with at least seven of the nasalis, orbicularis oculi, frontalis, corrugator, procerus, masseter, occipitalis, temporalis, trapezius and cervical paraspinal muscle regions. By avoiding certain administration locations, side effects can be lessened or eliminated.

For example, disclosed embodiments comprise administration to the nasalis, or the nasalis and corrugator, or the nasalis and corrugator and procerus, or the nasalis corrugator and procerus and occipitalis, or the nasalis and corrugator and procerus and occipitalis and temporalis, or the nasalis and corrugator and procerus and occipitalis and temporalis and trapezius and orbicularis oculi, or the nasalis and corrugator and procerus and occipitalis and temporalis and trapezius, or the corrugator and procerus and occipitalis and temporalis and trapezius and masseter muscle regions.

Further embodiments for treating EM comprise an injection protocol as described in Table 1:

|  | Sensory Targets | Nr Sites/ Side | Total Sites | Type of Injection | Dose/Site | Total Dose |
|---|---|---|---|---|---|---|
| Trapezius |  | 2 (superior and inferior) | 4 | Superficial IM (Superior) IM (Inferior) | 5U (Superior) 10U (Inferior) | 10U 20U |
| Occipitalis |  | 3 | 6 | IM | 10U | 60U |
| Temporalis |  | 3 (anterior to tragus) | 6 | IM | 5U | 30U |
| Procerus |  | 1 | 1 | IM | 5U | 5U |
| Corrugator |  | 1 | 2 | IM | 5U | 10U |
| Oculi |  | 1 | 2 | IM | 5U | 10U |
| Total |  | 11 | 21 |  |  | 145U |

In Table 1, "Nr Sites/Side" means number of sites per side of head. "SD" means subdermal injection, "IM" means intramuscular injection, "SQ" means subcutaneous injection. The protocol of Table 1 can be adjusted based on treatment goals and results. For example, the number of injection locations to the trapezius per side (superior [reference numeral 2 in FIG. 4] and inferior [reference numeral 1 in FIG. 4]) can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the trapezius (superior and inferior) can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the superior trapezius can be subdermal as described on Table 1 or superficial intramuscular injections as described on Table 2. The injections to the inferior trapezius can be intramuscular as described on Table 1 and Table 2.

The dosage per injection site to the trapezius (superior and inferior) can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the trapezius (superior and inferior) can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

Figure 4:
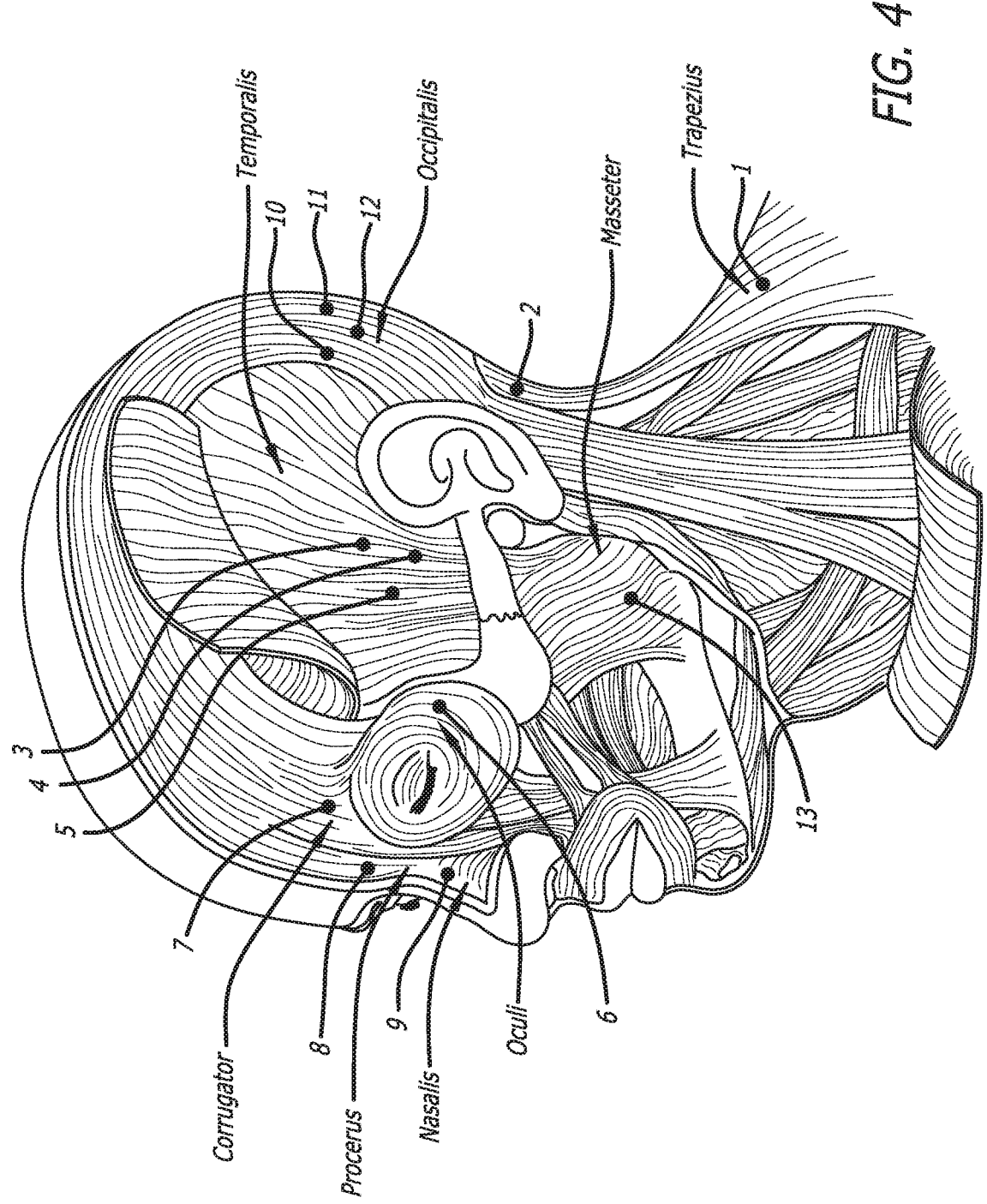
FIG. 4 shows the approximate location of several injection sites in various muscle regions as disclosed herein.

In the embodiments of Table 1, the number of injections to the occipitalis per side (reference numerals 10, 11, and 12 in FIG. 4; mid-point of nuchal ridge for the first injection, which is done above the ridge. In embodiments the second and third injections form an inverted triangle with the first, and there is a about 2-3 cm between each injection point) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the occipitalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the occipitalis can be, for example, 5 units, 10 units, 15 units, 20 units, between 5 and 20 units, between 5 and 15 units, between 5 and 10 units, between 10 and 15 units, or the like.

The total dosage to the occipitalis can be, for example, 20 units, 25 units, 30 units, 35 units, 40 units, 45 units, 50 units, 55 units, 60 units, 65 units, 70 units, 75 units, 80 units, 85 units, or between 20 and 40 units, between 25 and 35 units, 35 and 80 units, between 35 and 65 units, between 45 and 70 units, between 50 and 80 units, between 40 and 85 units, between 50 and 70 units, between 55 and 65 units, between 45 and 70 units, between 55 and 75 units, between 65 and 80 units, or the like.

In the embodiments of Table 1, the number of injections to the temporalis per side (reference numerals 3, 4, and 5 in FIG. 4) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the temporalis, can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the temporalis can be, for example, 2 units, 3 units, 4 units, 5 units, 10 units, 15 units, 20 units, between 2 and 10 units, between 4 and 8 units, between 4 and 6 units, between 5 and 20 units, between 5 and 15 units, between 5 and 10 units, between 10 and 15 units, or the like.

The total dosage to the temporalis can be, for example, 15 units, 20 units, 25 units, 30 units, 35 units, 40 units, 45 units, 50 units, 55 units, 60 units, or the like, or between 15 and 60 units, between 20 and 55 units, between 25 and 50 units, between 20 and 40 units, between 25 and 35 units, or the like.

In the embodiments of Table 1, the number of injections to the procerus (reference numeral 8 in FIG. 4) can be 1, 2, 3, 4, 5, or the like, or between 1 and 5 injections, between 1 and 4 injections, between 1 and 3 injections, between 2 and 5 injections, between 2 and 4 injections, between 1 and 3 injections, or the like.

The dosage per injection site to the procerus can be, for example, 3 units, 4 units, 5 units, 6 units, 7 units, 8 units, between 1 and 7 units, between 2 and 6 units, between 3 and 5 units, between 4 and 6 units, or the like.

The total dosage to the procerus can be, for example, 3 units, 4 units, 5 units, 6 units, 7 units, 8 units, between 1 and 7 units, between 2 and 6 units, between 3 and 5 units, between 4 and 6 units, or the like.

In the embodiments of Table 1, the number of injections to the corrugator per side (reference numeral 7 in FIG. 4) can be 1, 2, 3, 4, or the like, or between 1 and 4 injections, between 1 and 3 injections, between 2 and 4 injections, or the like. The injections to the corrugator can be parallel to the muscle. The injections to the corrugator can be to multiple total sites, for example, 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the corrugator can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the corrugator can be, for example, 3 units, 4 units, 5 units, 6 units, 7 units, 8 units, 9 units, 10 units, 11 units, 12 units, 13 units, 14 units, 15 units, 16 units, between 3 and 16 units, between 3 and 14 units, between 3 and 12 units, between 4 and 16 units, between 5 and 15 units, between 6 and 14 units, between 7 and 13 units, between 8 and 12 units, between 9 and 11 units, or the like.

In the embodiments of Table 1, the number of injections to the oculi per side (reference numeral 6 in FIG. 4) can be 1, 2, 3, 4, or the like, or between 1 and 4 injections, between 1 and 3 injections, between 2 and 4 injections, or the like. The injections to the oculi can be to multiple total sites, for example 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the oculi can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the oculi can be, for example, 2, 3 units, 4 units, 5 units, 6 units, 7 units, 8 units, 9 units, 10 units, 11 units, 12 units, 13 units, 14 units, 15 units, 16 units, 17, 18, 19, and 20, between 2 and 20 units, between 4 and 18 units, between 6 and 16 units, between 8 and 14 units, between 8 and 12 units, between 9 and 11 units, or the like.

Further embodiments for treating EM comprise an injection protocol as seen in Table 2:

| Sensory Targets | Nr Sites/Side | Total Sites | Type of Injection | Dose/Site | Total Dose |
| --- | --- | --- | --- | --- | --- |
| Trapezius | 2 (superior and inferior) | 4 | Superficial IM (Superior) IM (Inferior) | 5U (Superior) 10U (Inferior) | 10U 20U |
| Occipitalis | 3 | 6 | IM | 10U | 60U |
| Temporalis | 3 (anterior to tragus) | 6 | IM | 5U | 30U |
| Procerus | 1 | 1 | IM | 5U | 5U |
| Corrugator | 1 | 2 | IM | 5U | 10U |
| Oculi | 1 | 2 | IM | 5U | 10U |
| Total | 11 | 21 | | | 145U |

In Table 2, "Nr Sites/Side" means number of sites per side of head. "Superficial IM" means superficial intramuscular injection, "IM" means intramuscular injection.

The protocol of Table 2 can be adjusted based on treatment goals and results. For example, the number of injection locations to the trapezius per side (superior [reference numeral 2 in FIG. 4] and inferior [reference numeral 1 in FIG. 4]) can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the trapezius (superior and inferior) can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the superior trapezius can be subdermal as described on Table 1 or superficial intramuscular injections as described on Table 2. The injections to the inferior trapezius can be intramuscular as described on Table 1 and Table 2.

The dosage per injection site to the trapezius (superior and inferior) can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the trapezius (superior and inferior) can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

In the embodiments of Table 2, the number of injections to the occipitalis per side (reference numerals 10, 11, and 12 in FIG. 4; mid-point of nuchal ridge for the first injection, which is done above the ridge. In embodiments the second and third injections form an inverted triangle with the first, and there is about 2-3 cm between each injection point) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the occipitalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the occipitalis can be, for example, 5 units, 10 units, 15 units, 20 units, between 5 and 20 units, between 5 and 15 units, between 5 and 10 units, between 10 and 15 units, or the like.

The total dosage to the occipitalis can be, for example, 20 units, 25 units, 30 units, 35 units, 40 units, 45 units, 50 units, 55 units, 60 units, 65 units, 70 units, 75 units, 80 units, 85 units, or between 20 and 40 units, between 25 and 35 units, between 35 and 80 units, between 35 and 65 units, between 45 and 70 units, between 50 and 80 units, between 40 and 85 units, between 50 and 70 units, between 55 and 65 units, between 45 and 70 units, between 55 and 75 units, between 65 and 80 units, or the like.

In the embodiments of Table 2, the number of injections to the temporalis per side (reference numerals 3, 4, and 5 in FIG. 4) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the temporalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the temporalis can be, for example, 2 units, 3 units, 4 units, 5 units, 10 units, 15 units, 20 units, between 2 and 10 units, between 4 and 8 units, between 4 and 6 units, between 5 and 20 units, between 5 and 15 units, between 5 and 10 units, between 10 and 15 units, or the like.

The total dosage to the temporalis can be, for example, 15 units, 20 units, 25 units, 30 units, 35 units, 40 units, 45 units, 50 units, 55 units, 60 units, or the like, or between 15 and 60 units, between 20 and 55 units, between 25 and 50 units, between 20 and 40 units, between 25 and 35 units, or the like.

In the embodiments of Table 2, the number of injections to the procerus (reference numeral 8 in FIG. 4) can be 1, 2, 3, 4, 5, or the like, or between 1 and 5 injections, between 1 and 4 injections, between 1 and 3 injections, between 2 and 5 injections, between 2 and 4 injections, between 1 and 3 injections, or the like.

The dosage per injection site to the procerus can be, for example, 3 units, 4 units, 5 units, 6 units, 7 units, 8 units, between 1 and 7 units, between 2 and 6 units, between 3 and 5 units, between 4 and 6 units, or the like.

The total dosage to the procerus can be, for example, 3 units, 4 units, 5 units, 6 units, 7 units, 8 units, between 1 and 7 units, between 2 and 6 units, between 3 and 5 units, between 4 and 6 units, or the like.

In the embodiments of Table 2, the number of injections to the corrugator (reference numeral 7 in FIG. 4) per side can be 1, 2, 3, 4, or the like, or between 1 and 4 injections, between 1 and 3 injections, between 2 and 4 injections, or the like. The injections to the corrugator can be parallel to the muscle. The injections to the corrugator can be to multiple total sites, for example, 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the corrugator can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the corrugator can be, for example, 3 units, 4 units, 5 units, 6 units, 7 units, 8 units, 9 units, 10 units, 11 units, 12 units, 13 units, 14 units, 15 units, 16 units, between 3 and 16 units, between 3 and 14 units, between 3 and 12 units, between 4 and 16 units, between 5 and 15 units, between 6 and 14 units, between 7 and 13 units, between 8 and 12 units, between 9 and 11 units, or the like.

In the embodiments of Table 2, the number of injections to the oculi (reference numeral 6 in FIG. 4) per side can be 1, 2, 3, 4, or the like, or between 1 and 4 injections, between 1 and 3 injections, between 2 and 4 injections, or the like. The injections to the oculi can be to multiple total sites, for example 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the oculi can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the oculi can be, for example, 2, 3 units, 4 units, 5 units, 6 units, 7 units, 8 units, 9 units, 10 units, 11 units, 12 units, 13 units, 14 units, 15 units, 16 units, 17, 18, 19, and 20, between 2 and 20 units, between 4 and 18 units, between 6 and 16 units, between 8 and 14 units, between 8 and 12 units, between 9 and 11 units, or the like.

Further embodiments for treating CM comprise an injection protocol as seen in Table 3:

|  | Targeted Nerves/ Nerve Pathways | Nr Sites/ Side | Total Sites | Type of Injection | Dose/Site | Total Dose |
|---|---|---|---|---|---|---|
| Trapezius | Suprascapular | 2 (superior and inferior) | 4 | SD (Superior) IM (Inferior) | 5U (Superior) 10U (Inferior) | 10U 20U |
| Occipitalis | Greater & Lesser occipital nerves | 3 | 6 | IM | 10U | 60U |
| Temporalis | Auriculotemporal | 3 (anterior to tragus) | 6 | IM | 10U | 60U |
| Procerus | Supratrochlear and supra-orbital | 1 | 1 | IM | 5U | 5U |
| Corrugator | Supratrochlear and supra-orbital | 1 | 2 | IM | 5U | 10U |
| Oculi | Zygomatic-temporal branch | 1 | 2 | IM | 5U | 10U |
| Nasalis | Nasociliary branch of infra-orbital | 1 | 2 | SQ | 2.5U | 5U |
| Masseter | Trigeminal motor division | 1 | 2 | IM | 5U | 10U |
| Total |  | 13 | 25 |  |  | 190U |

In Table 3, "Nr Sites/Side" means number of sites per side of head. "SD" means subdermal injection, "IM" means intramuscular injection, "SQ" means subcutaneous injection. The protocol of Table 3 can be adjusted based on treatment goals and results. For example, the number of injection locations to the trapezius per side (superior [reference numeral 2 in FIG. 4] and inferior [reference numeral 1 in FIG. 4]) can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the trapezius (superior and inferior) can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the superior trapezius can be subdermal as described on Table 3 or superficial intramuscular injections as described in Table 4. The injections to the inferior trapezius can be intramuscular as described in Table 3 and Table 4.

The dosage per injection site to the trapezius (superior and inferior) can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the trapezius (superior and inferior) can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

In the embodiments of Table 3, the number of injections to the occipitalis per side (reference numerals 10, 11, and 12 in FIG. 4; mid-point of nuchal ridge for the first injection, which is done above the ridge. In embodiments the second and third injections form an inverted triangle with the first, and there is a about 2-3 cm between each injection point) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the occipitalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the occipitalis can be, for example, 5 units, 10 units, 15 units, 20 units, between 5 and 20 units, between 5 and 15 units, between 5 and 10 units, between 10 and 15 units, or the like.

The total dosage to the occipitalis can be, for example, 20 units, 25 units, 30 units, 35 units, 40 units, 45 units, 50 units, 55 units, 60 units, 65 units, 70 units, 75 units, 80 units, 85 units, or between 20 and 40 units, between 25 and 35 units, 35 and 80 units, between 35 and 65 units, between 45 and 70 units, between 50 and 80 units, between 40 and 85 units, between 50 and 70 units, between 55 and 65 units, between 45 and 70 units, between 55 and 75 units, between 65 and 80 units, or the like.

In the embodiments of Table 3, the number of injections to the temporalis per side (reference numerals 3, 4, and 5 in FIG. 4) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the temporalis, can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the temporalis can be, for example, 2 units, 3 units, 4 units, 5 units, 10 units, 15 units, 20 units, between 2 and 10 units, between 4 and 8 units, between 4 and 6 units, between 5 and 20 units, between 5 and 15 units, between 5 and 10 units, between 10 and 15 units, between 8 and 12 units, between 9 and 11 units, or the like.

The total dosage to the temporalis can be, for example, 15 units, 20 units, 25 units, 30 units, 35 units, 40 units, 45 units, 50 units, 55 units, 60 units, 65 units, 70 units, 75 units, 80 units, or the like, or between 20 and 80 units, between 25 and 75 units, between 30 and 70 units, between 35 and 65 units, between 50 and 70, between 55 and 65 units, or the like.

In the embodiments of Table 3, the number of injections to the procerus (reference numeral 8 in FIG. 4) can be 1, 2, 3, 4, 5, or the like, or between 1 and 5 injections, between 1 and 4 injections, between 1 and 3 injections, between 2 and 5 injections, between 2 and 4 injections, between 1 and 3 injections, or the like.

The dosage per injection site to the procerus can be, for example, 3 units, 4 units, 5 units, 6 units, 7 units, 8 units, between 1 and 7 units, between 2 and 6 units, between 3 and 5 units, between 4 and 6 units, or the like.

The total dosage to the procerus can be, for example, 3 units, 4 units, 5 units, 6 units, 7 units, 8 units, between 1 and 7 units, between 2 and 6 units, between 3 and 5 units, between 4 and 6 units, or the like.

In the embodiments of Table 3, the number of injections to the corrugator (reference numeral 7 in FIG. 4) per side can be 1, 2, 3, 4, or the like, or between 1 and 4 injections, between 1 and 3 injections, between 2 and 4 injections, or the like. The injections to the corrugator can be parallel to the muscle. The injections to the corrugator can be to multiple total sites, for example, 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the corrugator can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the corrugator can be, for example, 3 units, 4 units, 5 units, 6 units, 7 units, 8 units, 9 units, 10 units, 11 units, 12 units, 13 units, 14 units, 15 units, 16 units, between 3 and 16 units, between 3 and 14 units, between 3 and 12 units, between 4 and 16 units, between 5 and 15 units, between 6 and 14 units, between 7 and 13 units, between 8 and 12 units, between 9 and 11 units, or the like.

In the embodiments of Table 3, the number of injections to the oculi (reference numeral 6 in FIG. 4) per side can be 1, 2, 3, 4, or the like, or between 1 and 4 injections, between 1 and 3 injections, between 2 and 4 injections, or the like. The injections to the oculi can be to multiple total sites, for example 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the oculi can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the oculi can be, for example, 2, 3 units, 4 units, 5 units, 6 units, 7 units, 8 units, 9 units, 10 units, 11 units, 12 units, 13 units, 14 units, 15 units, 16 units, 17, 18, 19, and 20, between 2 and 20 units, between 4 and 18 units, between 6 and 16 units, between 8 and 14 units, between 8 and 12 units, between 9 and 11 units, or the like.

In the embodiments of Table 3, the number of subcutaneous injections per side to the nasalis (reference numeral 9 in FIG. 4) can be 1, 2, 3 or the like, or between 1 and 3 injections, or the like. The injections to the nasalis can be subcutaneous as described in Table 3 or superficial intramuscular as described in Table 4.

In the embodiments of Table 3, the total number of subcutaneous injections to the nasalis can be 1, 2, 3, 4, 5, 6, or the like, or between 1 and 6 injections, between 1 and 3 injections, between 2 and 4 injections, between 3 and 5, between 4 and 6, between 1 and 4, or the like.

The dosage per subcutaneous injection site to the nasalis can be, for example, 1 unit, 1.5 units 2 units, 2.5 units, 3 units, 3.5 units, 4 units, 4.5 units, 5 units, between 1 and 5 units, between 2 and 4 units, between 2 and 3 units, or the like.

The total subcutaneous dosage to the nasalis can be, for example, 2 units, 3 units, 4 units, 5 units, 6 units, 7 units, 8 units, 9 units, 10 units, between 2 and 10 units, between 3 and 9 units, between 4 and 8 units, between 4 and 6 units, between 5 and 10 units, between 5 and 8 units, or the like.

In the embodiments of Table 3, the number of injections per side to the masseter can be 1, 2, 3, 4, or the like, or between 1 and 4 injections, between 1 and 3 injections, between 2 and 4 injections, or the like.

In the embodiments of Table 3, the total number of injections to the masseter (reference numeral 13 in FIG. 4) can be 1, 2, 3, 4, 5, 6, 7, 8, or the like, or between 1 and 4 injections, between 1 and 3 injections, between 2 and 4 injections, between 4 and 6, between 4 and 8, or the like.

The dosage per injection site to the masseter can be, for example, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the masseter can be, for example, 4 units, 5 units, 6 units, 7 units, 8 units, 9 units, 10 units, 11 units, 12 units, 13 units, 14 units, 15 units, 16 units, 17 units, 18 units, 19 units, 20 units, between 4 and 20 units, between 6 and 18 units, between 8 and 16 units, between 10 and 14 units, between 8 and 12 units, between 9 and 11 units, or the like.

Further embodiments for treating CM comprise an injection protocol as seen in Table 4:

| Sensory Targets | Nr Sites/ Side | Total Sites | Type of Injection | Dose/Site | Total Dose |
|---|---|---|---|---|---|
| Trapezius | 2 (superior and inferior) | 4 | Superficial IM (Superior) IM (Inferior) | 5U (Superior) 10U (Inferior) | 10U 20U |
| Occipitalis | 3 | 6 | IM | 10U | 60U |
| Temporalis | 3 (anterior to tragus) | 6 | IM | 10U | 60U |
| Procerus | 1 | 1 | IM | 5U | 5U |
| Corrugator | 1 | 2 | IM | 5U | 10U |
| Oculi | 1 | 2 | IM | 5U | 10U |
| Nasatis: | 1 | 2 | Superficial IM | 2.5U | 5U |
| Masseter | 1 | 2 | IM | 5U | 10U |
| Total | 13 | 25 | | | 190U |

In Table 4, "Nr Sites/Side" means number of sites per side of head. "Superficial IM" means superficial intramuscular injection, "IM" means intramuscular injection. The protocol of Table 4 can be adjusted based on treatment goals and results. For example, the number of injection locations to the trapezius per side (superior [reference numeral 2 in FIG. 4] and inferior [reference numeral 1 in FIG. 4]) can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the trapezius (superior and inferior) can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the superior trapezius can be subdermal as described on Table 3 or superficial intramuscular injections as described on Table 4. The injections to the inferior trapezius can be intramuscular as described on Table 3 and Table 4.

The dosage per injection site to the trapezius (superior and inferior) can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the trapezius (superior and inferior) can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

In the embodiments of Table 4, the number of injections to the occipitalis per side (reference numerals 10, 11, and 12 in FIG. 4; mid-point of nuchal ridge for the first injection, which is done above the ridge. In embodiments the second and third injections form an inverted triangle with the first, and there is a about 2-3 cm between each injection point) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the occipitalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the occipitalis can be, for example, 5 units, 10 units, 15 units, 20 units, between 5 and 20 units, between 5 and 15 units, between 5 and 10 units, between 10 and 15 units, or the like.

The total dosage to the occipitalis can be, for example, 20 units, 25 units, 30 units, 35 units, 40 units, 45 units, 50 units, 55 units, 60 units, 65 units, 70 units, 75 units, 80 units, 85 units, or between 20 and 40 units, between 25 and 35 units, 35 and 80 units, between 35 and 65 units, between 45 and 70 units, between 50 and 80 units, between 40 and 85 units, between 50 and 70 units, between 55 and 65 units, between 45 and 70 units, between 55 and 75 units, between 65 and 80 units, or the like.

In the embodiments of Table 4, the number of injections to the temporalis per side (reference numerals 3, 4, and 5 in FIG. 4) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the temporalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the temporalis can be, for example, 2 units, 3 units, 4 units, 5 units, 10 units, 15 units, 20 units, between 2 and 10 units, between 4 and 8 units, between 4 and 6 units, between 5 and 20 units, between 5 and 15 units, between 5 and 10 units, between 10 and 15 units, between 8 and 12 units, between 9 and 11 units, or the like.

The total dosage to the temporalis can be, for example, 15 units, 20 units, 25 units, 30 units, 35 units, 40 units, 45 units, 50 units, 55 units, 60 units, 65 units, 70 units, 75 units, 80 units, or the like, or between 20 and 80 units, between 25 and 75 units, between 30 and 70 units, between 35 and 65 units, between 50 and 70, between 55 and 65 units, or the like.

In the embodiments of Table 4, the number of injections to the procerus (reference numeral 8 in FIG. 4) can be 1, 2, 3, 4, 5, or the like, or between 1 and 5 injections, between 1 and 4 injections, between 1 and 3 injections, between 2 and 5 injections, between 2 and 4 injections, between 1 and 3 injections, or the like.

The dosage per injection site to the procerus can be, for example, 3 units, 4 units, 5 units, 6 units, 7 units, 8 units, between 1 and 7 units, between 2 and 6 units, between 3 and 5 units, between 4 and 6 units, or the like.

The total dosage to the procerus can be, for example, 3 units, 4 units, 5 units, 6 units, 7 units, 8 units, between 1 and 7 units, between 2 and 6 units, between 3 and 5 units, between 4 and 6 units, or the like.

In the embodiments of Table 4, the number of injections to the corrugator (reference numeral 7 in FIG. 4) per side can be 1, 2, 3, 4, or the like, or between 1 and 4 injections, between 1 and 3 injections, between 2 and 4 injections, or the like. The injections to the corrugator can be parallel to the muscle. The injections to the corrugator can be to multiple total sites, for example, 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the corrugator can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the corrugator can be, for example, 3 units, 4 units, 5 units, 6 units, 7 units, 8 units, 9 units, 10 units, 11 units, 12 units, 13 units, 14 units, 15 units, 16 units, between 3 and 16 units, between 3 and 14 units, between 3 and 12 units, between 4 and 16 units, between 5 and 15 units, between 6 and 14 units, between 7 and 13 units, between 8 and 12 units, between 9 and 11 units, or the like.

In the embodiments of Table 4, the number of injections to the oculi (reference numeral 6 in FIG. 4) per side can be 1, 2, 3, 4, or the like, or between 1 and 4 injections, between 1 and 3 injections, between 2 and 4 injections, or the like. The injections to the oculi can be to multiple total sites, for example 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the oculi can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the oculi can be, for example, 2 units, 3 units, 4 units, 5 units, 6 units, 7 units, 8 units, 9 units, 10 units, 11 units, 12 units, 13 units, 14 units, 15 units, 16 units, 17, 18, 19, and 20, between 2 and 20 units, between 4 and 18 units, between 6 and 16 units, between 8 and 14 units, between 8 and 12 units, between 9 and 11 units, or the like.

In the embodiments of Table 4, the number of superficial IM injections per side to the nasalis (reference numeral 9 in FIG. 4) can be 1, 2, 3 or the like, or between 1 and 3 injections, or the like. The injections to the nasalis can be subcutaneous as described in Table 3 or superficial intramuscular as described in Table 4.

In the embodiments of Table 4, the total number of superficial IM injections to the nasalis can be 1, 2, 3, 4, 5, 6, or the like, or between 1 and 6 injections, between 1 and 3 injections, between 2 and 4 injections, between 3 and 5, between 4 and 6, between 1 and 4, or the like.

The dosage per superficial IM injection site to the nasalis can be, for example, 1 unit, 1.5 units 2 units, 2.5 units, 3 units, 3.5 units, 4 units, 4.5 units, 5 units, between 1 and 5 units, between 2 and 4 units, between 2 and 3 units, or the like.

The total superficial IM dosage to the nasalis can be, for example, 2 units, 3 units, 4 units, 5 units, 6 units, 7 units, 8 units, 9 units, 10 units, between 2 and 10 units, between 3 and 9 units, between 4 and 8 units, between 4 and 6 units, between 5 and 10 units, between 5 and 8 units, or the like.

In the embodiments of Table 4, the number of injections (reference numeral 13 in FIG. 4) per side to the masseter can be 1, 2, 3, 4, or the like, or between 1 and 4 injections, between 1 and 3 injections, between 2 and 4 injections, or the like.

In the embodiments of Table 4, the total number of injections to the masseter can be 1, 2, 3, 4, 5, 6, 7, 8, or the like, or between 1 and 4 injections, between 1 and 3 injections, between 2 and 4 injections, between 4 and 6, between 4 and 8, or the like.

The dosage per injection site to the masseter can be, for example, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the masseter can be, for example, 4 units, 5 units, 6 units, 7 units, 8 units, 9 units, 10 units, 11 units, 12 units, 13 units, 14 units, 15 units, 16 units, 17 units, 18 units, 19 units, 20 units, between 4 and 20 units, between 6 and 18 units, between 8 and 16 units, between 10 and 14 units, between 8 and 12 units, between 9 and 11 units, or the like.

Further embodiments for treating CM comprise an injection protocol as seen in Table 5:

| Targeted Nerves/ Nerve Pathways | Muscles to Inject | Nr Sites/ Side | Total Sites | Type of Injection | Dose/Site | Total Dose |
| --- | --- | --- | --- | --- | --- | --- |
| Supra-orbital | Upper Frontalis | 1 (at hairline) | 2 | IM | 5U | 10U |
| Supratrochlear and Supra-Orbital | Corrugator | 1 | 2 | IM | 5U | 10U |
| Zygomatic-temporal branch | Oculi | 1 | 2 | IM | 5U | 10U |
| Auricular-temporal and Zygomatic-temporal branches | Temporalis | 3 (anterior to tragus) | 6 | IM | 5U | 30U |
| Greater & Lesser occipital nerves | Occipitalis | 3-2 | 6 | IM | 10U | 60U |

| Targeted Nerves/ Nerve Pathways | Muscles to Inject | Nr Sites/ Side | Total Sites | Type of Injection | Dose/Site | Total Dose |
| --- | --- | --- | --- | --- | --- | --- |
| 3rd Occipital nerve and Suprascapular | Trapezius | 2 (superior and inferior) | 4 | Superficial IM (Superior) IM (Inferior) | 5U (Superior) 10U (Inferior) | 10U 20U |
| Total | | 11 | 22 | | | 150U |

Figure 5:
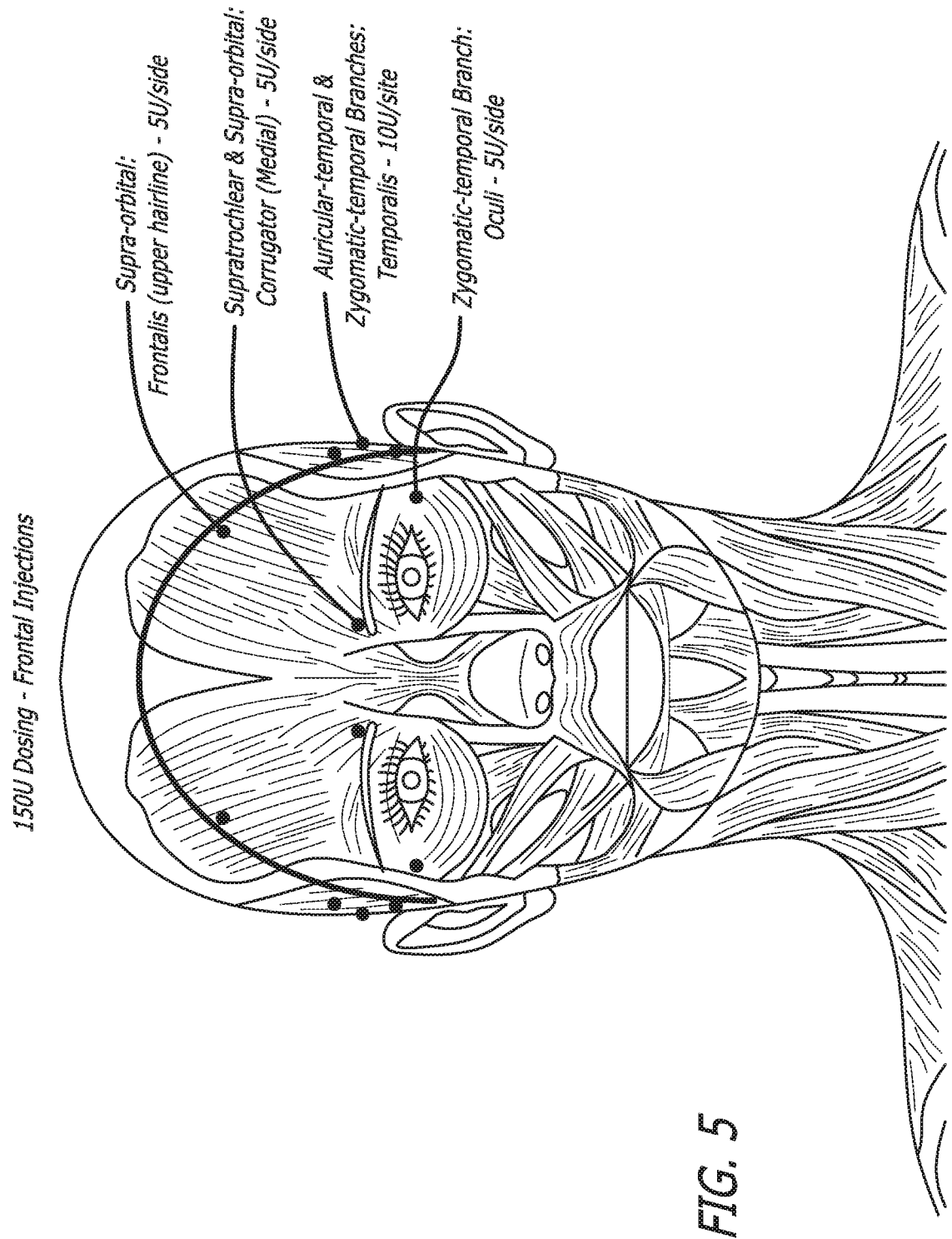
FIG. 5 shows the approximate frontal injection sites in various muscle regions used in a 150 Unit migraine treatment as described in Table 5 and the following paragraphs.
Figure 6:
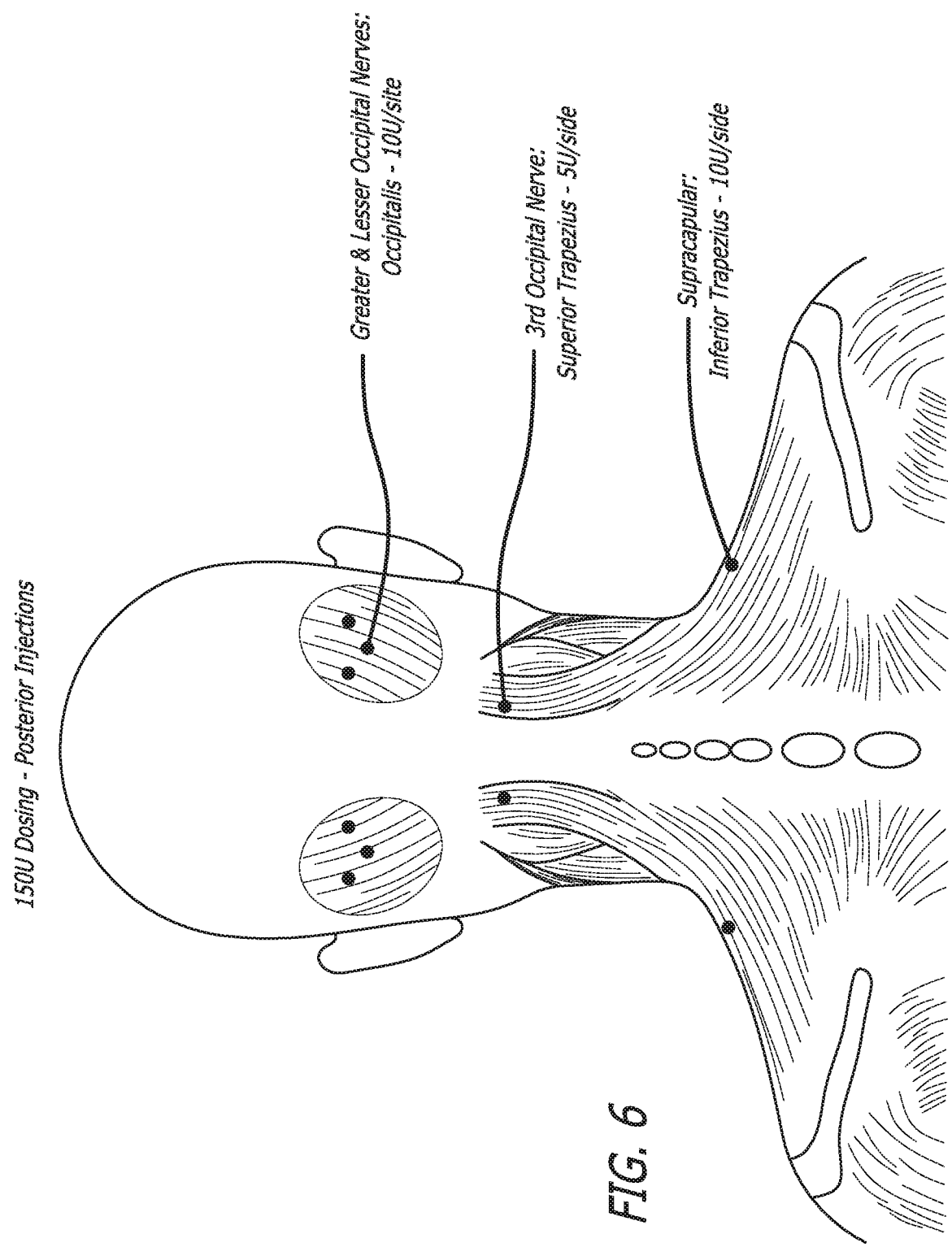
FIG. 6 shows the approximate posterior injection sites in various muscle regions used in a 150 Unit migraine treatment as described in Table 5 and the following paragraphs.

In Table 5, "Nr Sites/Side" means number of sites per side of head. "Superficial IM" means superficial intramuscular injection, "IM" means intramuscular injection. Injection locations associated with Table 5 are shown in FIGS. 5 and 6. In embodiments, injections directed toward the supraorbital nerve comprise upper frontalis injections at or near the hairline, comprising two lateral injections, one 5 unit injection in each side of the upper frontalis muscle for a total of 10 units. In some embodiments, the frontalis injection technique comprises starting at the limbic line where the forehead starts to angle backwards, injecting at a 45-degree angle, and angling away from the lower forehead.

In embodiments, injections directed toward the supratrochlear and supraorbital nerves comprise injecting the corrugator muscles near the medial line, utilizing 2 parallel linear threading approach injections, with one 5 unit injection in each side of the medial corrugator muscle for a total of 10 units. In embodiments, the injection technique comprises inserting the needle at the medial edge of the corrugator muscle (at the vertical crease line) and parallel to the orbital ridge horizontal plane (parallel to the muscle above the eyebrow) and perpendicular to the corrugator skin line. The needle is slightly angled to the skin coming in on the medial edge and the needle is inserted ½" while holding the muscle. The injector begins depressing the plunger as the needle is withdrawn towards the injection site and stops at the medial line. This "linear threading" approach allows for diffusion of the toxin into the area of the procerus and supratroclear nerve while minimizing the number of injections for the patient.

In embodiments, injections directed toward the nerves of the zygomatic-temporal branch comprise injection of the oculi area with one 5 unit injection on each side of the face to the lateral side of the oculi muscle for a total of 10 units. In embodiments, injections are made at a 45-degree angle to the face with only the bevel inserted, while avoiding any vascular structures that are visible.

In embodiments, injections directed toward the auricular-temporal and zygomatic-temporal branches comprise injecting the anterior temporalis area with three 5 unit or 10 unit injections in each side of the anterior temporalis area, anterior to the tragus, for a total of 30 units or 60 units. For the most anterior of the three temporal injections, the injections are made at the hairline, angling the needle back towards the hairline of the temporal area to avoid the antra-temporal fascia and to minimize atrophy in that region. The other temporal injections may be behind the hairline, parallel to the tragus and injected 45 degrees to the skull.

In embodiments, injections directed to the greater and lesser occipital nerves comprise injecting the occipitalis area with three 10 unit intramuscular injections in each occipitalis muscle for a total of 60 units. The injection technique comprises inserting the needle parallel to the nuchal ridge. The injector starts to depress the plunger as the needle is withdrawn towards the injection site (a parallel linear threading approach to maximize spread) and aims to inject the first half of the dose in the lateral region and the second half of the dose in the medial region. The "linear threading" approach should allow for diffusion of the toxin into the occipitalis area and greater and lesser occipital nerves and may allow for less injections in the occipitalis, for example, two injections per side versus three injections per side.

In embodiments, injections directed to the $3^{rd}$ occipital nerve and suprascapular nerve comprise injecting superficially into the superior and inferior trapezius areas with two intramuscular injections into each trapezius muscle, 5 units in the superior trapezius muscle and 10 units into the inferior trapezius muscle, for a total of 30 units. The injection technique for the superior trapezius injection comprises injecting upward away from the mid-neck toward the base of the skull at a 45-degree angle, angled toward the lower hairline, and parallel to the C2. The injector starts to depress the plunger as the needle is withdrawn towards the injection site (a parallel linear threading approach to maximize spread). For the inferior trapezius, the injection technique comprises injecting at a 45-degree angle at the top of the slope of the trapezius. The "linear threading" approach should allow for diffusion of the toxin into the superior trapezius area and $3^{rd}$ occipital nerve.

In certain embodiments, the method comprises injecting the composition sub-dermally, subcutaneously, intramuscularly, or through superficial intramuscular injections, into the individual. For example, administering may comprise injecting the composition through a 27 gauge needle, 28 gauge needle, 29 gauge needle, 30 gauge needle, 31 gauge needle, 32 gauge needle, and/or 33 gauge needle. In certain embodiments, the method comprises administering a composition comprising a botulinum toxin type A.

In embodiments, the administration comprises using a 32 gauge needle. In some embodiments, the administration comprises using a ½ inch long 32 gauge needle. In embodiments, the administration comprises using a 30 gauge needle. In some embodiments, the administration comprises using a ½ inch long 30 gauge needle.

The protocol of Table 5 can be adjusted based on treatment goals and results. For example, the number of injections to the upper frontalis at the hairline per side can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the upper frontalis can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the upper frontalis can be intramuscular injections as described in Table 5.

The dosage per injection site to the upper frontalis can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the upper frontalis can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

In the embodiments of Table 5, the number of injections to the corrugator per side (reference numeral 7 in FIG. 4) can be 1, 2, 3, 4, or the like, or between 1 and 4 injections, between 1 and 3 injections, between 2 and 4 injections, or the like. The injections to the corrugator can be parallel to the muscle. The injections to the corrugator can be to multiple total sites, for example, 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the corrugator can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the corrugator can be, for example, 3 units, 4 units, 5 units, 6 units, 7 units, 8 units, 9 units, 10 units, 11 units, 12 units, 13 units, 14 units, 15 units, 16 units, between 3 and 16 units, between 3 and 14 units, between 3 and 12 units, between 4 and 16 units, between 5 and 15 units, between 6 and 14 units, between 7 and 13 units, between 8 and 12 units, between 9 and 11 units, or the like.

In the embodiments of Table 5, the number of injections to the oculi (reference numeral 6 in FIG. 4) per side can be 1, 2, 3, 4, or the like, or between 1 and 4 injections, between 1 and 3 injections, between 2 and 4 injections, or the like. The injections to the oculi can be to multiple total sites, for example 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the oculi can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the oculi can be, for example, 2, 3 units, 4 units, 5 units, 6 units, 7 units, 8 units, 9 units, 10 units, 11 units, 12 units, 13 units, 14 units, 15 units, 16 units, 17, 18, 19, and 20, between 2 and 20 units, between 4 and 18 units, between 6 and 16 units, between 8 and 14 units, between 8 and 12 units, between 9 and 11 units, or the like.

In the embodiments of Table 5, the number of injections to the temporalis anterior to the tragus (reference numerals 3, 4, and 5 in FIG. 4) per side can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the temporalis, can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the temporalis can be, for example, 2 units, 3 units, 4 units, 5 units, 10 units, 15 units, 20 units, between 2 and 10 units, between 4 and 8 units, between 4 and 6 units, between 5 and 20 units, between 5 and 15 units, between 5 and 10 units, between 10 and 15 units, or the like.

The total dosage to the temporalis can be, for example, 15 units, 20 units, 25 units, 30 units, 35 units, 40 units, 45 units, 50 units, 55 units, 60 units, or the like, or between 15 and 60 units, between 20 and 55 units, between 25 and 50 units, between 20 and 40 units, between 25 and 35 units, or the like.

In the embodiments of Table 5, the number of injections to the occipitalis per side (reference numerals 10, 11, and 12 in FIG. 4; mid-point of nuchal ridge for the first injection, which is done above the ridge. In embodiments the second and third injections form an inverted triangle with the first, and there is about 2-3 cm between each injection point) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the occipitalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the occipitalis can be, for example, 5 units, 10 units, 15 units, 20 units, between 5 and 20 units, between 5 and 15 units, between 5 and 10 units, between 10 and 15 units, or the like.

The total dosage to the occipitalis can be, for example, 20 units, 25 units, 30 units, 35 units, 40 units, 45 units, 50 units, 55 units, 60 units, 65 units, 70 units, 75 units, 80 units, 85 units, or between 20 and 40 units, between 25 and 35 units, 35 and 80 units, between 35 and 65 units, between 45 and 70 units, between 50 and 80 units, between 40 and 85 units, between 50 and 70 units, between 55 and 65 units, between 45 and 70 units, between 55 and 75 units, between 65 and 80 units, or the like.

In the embodiments of Table 5, the number of injection locations to the trapezius per side (superior [reference numeral 2 in FIG. 4] and inferior [reference numeral 1 in FIG. 4]) can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the trapezius (superior and inferior) can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the superior trapezius can be subdermal as described on Table 3 or superficial intramuscular injections as described on Table 4. The injections to the inferior trapezius can be intramuscular as described on Table 3 and Table 4.

The dosage per injection site to the trapezius (superior and inferior) can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the trapezius (superior and inferior) can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

Further embodiments for treating CM comprise an injection protocol as seen in Table 6:

| Targeted Nerves/ Nerve Pathways | Muscles to Inject | Nr Sites/ Side | Total Sites | Type of Injection | Dose/Site | Total Dose |
|---|---|---|---|---|---|---|
| Supra-orbital | Upper Frontalis | 1 (at hairline) | 2 | IM | 5U | 10U |
| Supratrochlear and Supra-Orbital | Corrugator | 1 | 2 | IM | 5U | 10U |
| Zygomatic-temporal branch | Oculi | 1 | 2 | IM | 5U | 10U |
| Auricular-temporal and Zygomatic-temporal branches | Temporalis | 3 (anterior to tragus) | 6 | IM | 10U | 60U |
| Nasociliary branch of infra-orbital | Nasalis | 1 | 2 | Superficial IM | 2.5U | 5U |
| Trigeminal motor division | Masseter | 1 | 2 | IM | 5U | 10U |
| Greater & Lesser occipital nerves | Occipitalis | 3 | 6 | IM | 10U | 60U |
| 3rd Occipital nerve and Suprascapular | Trapezius | 2 (superior and inferior) | 4 | Superficial IM (superior) IM (inferior) | 5U (Superior) 10U (Inferior) | 10U 20U |
| Total | | 13 | 26 | | | 195U |

Figure 7:
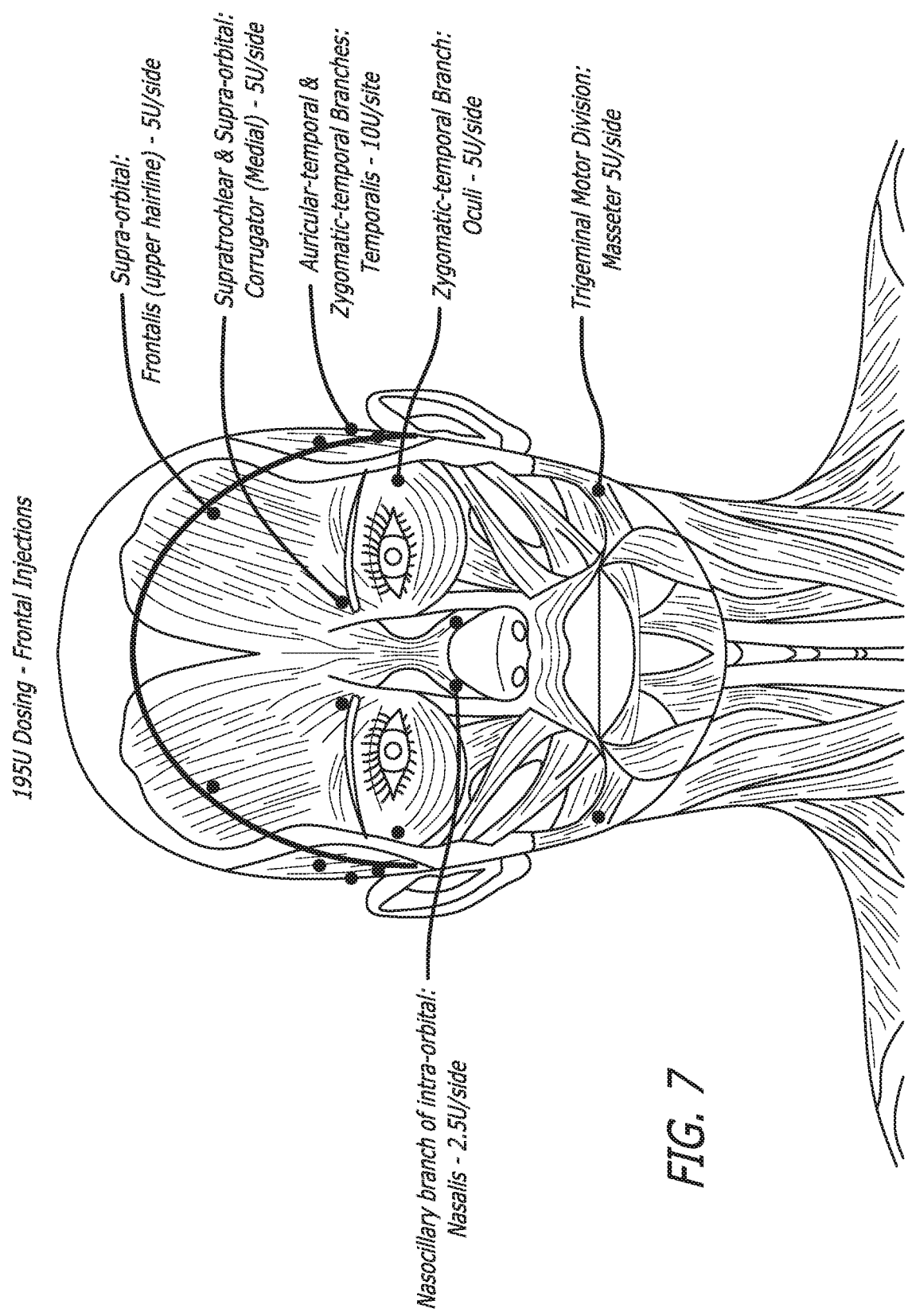
FIG. 7 shows the approximate frontal injection sites in various muscle regions used in a 195 Unit migraine treatment as described in Table 6 and the following paragraphs.
Figure 8:
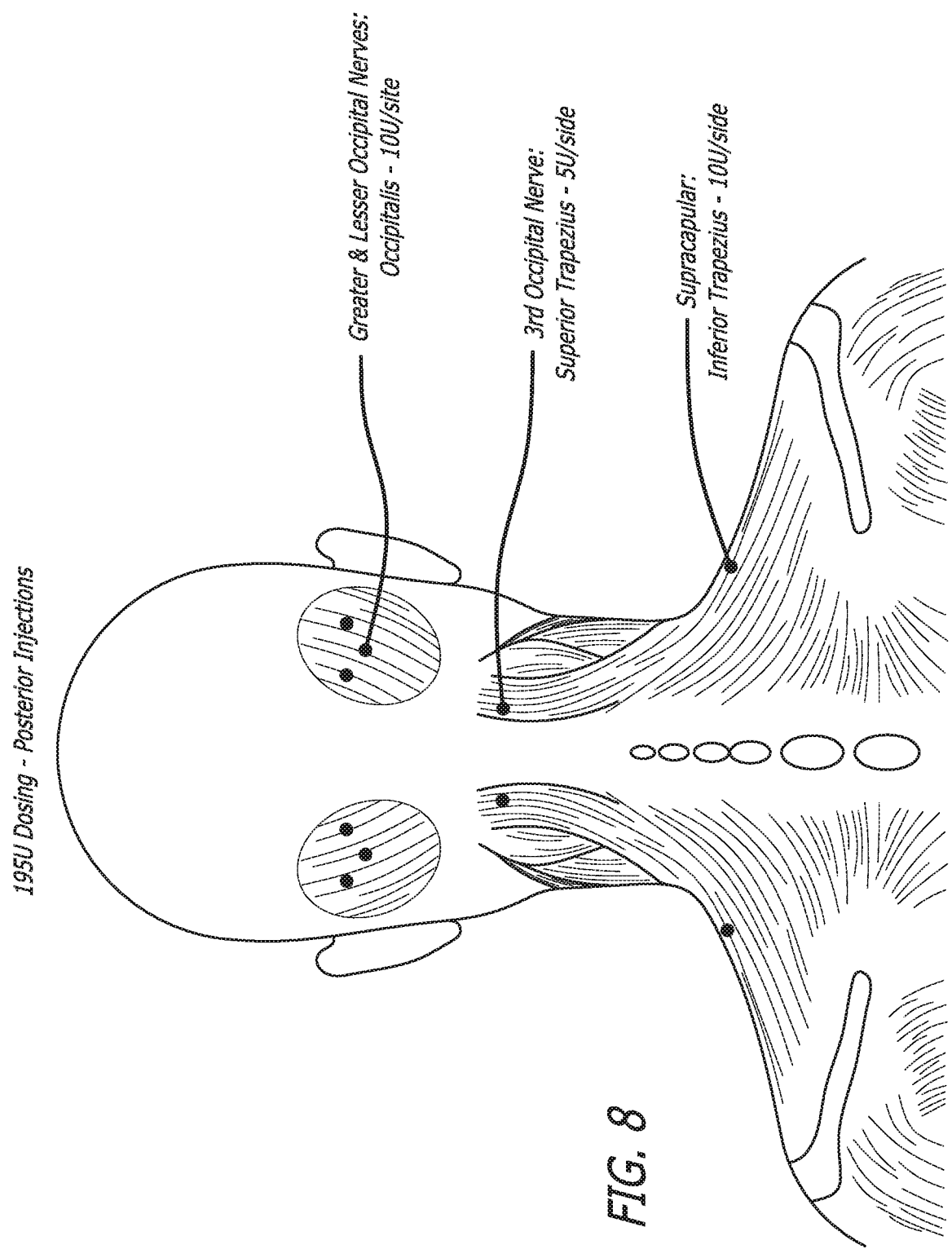
FIG. 8 shows the approximate posterior injection sites in various muscle regions used in a 195 Unit migraine treatment as described in Table 6 and the following paragraphs.

In Table 6, "Nr Sites/Side" means number of sites per side of head. "Superficial IM" means superficial intramuscular injection, "IM" means intramuscular injection. Injection locations associated with Table 6 are shown in FIGS. 7 and 8. In embodiments, injections directed toward the supraorbital nerve comprise upper frontalis injections at or near the hairline, comprising two lateral injections, one 5 unit injection in each side of the upper frontalis muscle for a total of 10 units. In some embodiments, the frontalis injection technique comprises starting at the limbic line where the forehead starts to angle backwards, injecting at a 45-degree angle, and angling away from the lower forehead.

In embodiments, injections directed toward the supratrochlear and supraorbital nerves comprise injecting the corrugator muscles near the medial line, utilizing 2 parallel linear threading approach injections, with one 5 unit injection in each side of the medial corrugator muscle for a total of 10 units.

In embodiments, the injection technique comprises inserting the needle at the medial edge of the corrugator muscle (at the vertical crease line) and parallel to the orbital ridge horizontal plane (parallel to the muscle above the eyebrow) and perpendicular to the corrugator skin line. The needle is slightly angled to the skin coming in on the medial edge and the needle is inserted ½" while holding the muscle. The injector begins depressing the plunger as the needle is withdrawn towards the injection site and stops at the medial line. This "linear threading" approach allows for diffusion of the toxin into the area of the procerus and supratroclear nerve while minimizing the number of injections for the patient.

In embodiments, injections directed toward the nerves of the zygomatic-temporal branch comprise injection of the oculi area with one 5 unit injection on each side of the face for a total of 10 units. In embodiments, injections are made at a 45-degree angle to the face with only the bevel inserted, while avoiding any vascular structures that are visible.

In embodiments, injections directed toward the auricular-temporal and zygomatic-temporal branches comprise injecting the anterior temporalis area with three 5 unit or 10 unit injections in each side of the anterior temporalis area, anterior to the tragus, for a total of 30 units or 60 units. For the most anterior of the three temporal injections, the injections are made at the hairline, angling the needle back towards the hairline of the temporal area to avoid the antra-temporal fascia and to minimize atrophy in that region. The other temporal injections may be behind the hairline, parallel to the tragus and injected 45 degrees to the skull.

In embodiments, injections directed toward the nasociliary branch of the infra-orbital nerve comprise injecting the nasalis area with one 2.5 unit superficial intramuscular injection in each side of the nasalis muscle, for a total of 5 units. The injection technique comprises inserting the needle at a 45-degree angle to the nose and inserting only the bevel of the needle.

In embodiments, injections directed toward the nerves of the trigeminal motor division comprise injecting the masseter area with one 5 unit intramuscular injection in each masseter muscle, for a total of 10 units. The injection technique comprises inserting the needle at a 45-degree angle.

In embodiments, injections directed to the greater and lesser occipital nerves comprise injecting the occipitalis area with three 10 unit intramuscular injections in each occipitalis muscle for a total of 60 units. The injection technique comprises inserting the needle parallel to the nuchal ridge. The injector starts to depress the plunger as the needle is withdrawn towards the injection site (a parallel linear threading approach to maximize spread) and aims to inject the first half of the dose in the lateral region and the second half of the dose in the medial region. The "linear threading" approach should allow for diffusion of the toxin into the occipitalis area and greater and lesser occipital nerves and may allow for less injections in the occipitalis, for example, two injections per side versus three injections per side.

In embodiments, injections directed to the $3^{rd}$ occipital nerve and suprascapular nerve comprise injecting the superior and inferior trapezius areas with two intramuscular injections into each trapezius muscle, 5 units superficially in the superior trapezius muscle and 10 units into the inferior trapezius muscle, for a total of 30 units. The injection technique for the superior trapezius injection comprises injecting upward away from the mid-neck toward the base of the skull at a 45-degree angle, angled toward the lower hairline, and parallel to the C2. The injector starts to depress the plunger as the needle is withdrawn towards the injection site (a parallel linear threading approach to maximize spread). For the inferior trapezius, the injection technique comprises injecting at a 45-degree angle at the top of the slope of the trapezius. The "linear threading" approach should allow for diffusion of the toxin into the superior trapezius area and $3^{rd}$ occipital nerve.

In certain embodiments, the method comprises injecting the composition sub-dermally, subcutaneously, intramuscularly, or through superficial intramuscular injections, into the individual. For example, administering may comprise injecting the composition through a 27 gauge needle, 28 gauge needle, 29 gauge needle, 30 gauge needle, 31 gauge needle, 32 gauge needle, and/or 33 gauge needle. In certain embodiments, the method comprises administering a composition comprising a botulinum toxin type A.

In embodiments, the administration comprises using a 32 gauge needle. In some embodiments, the administration comprises using a ½ inch long 32 gauge needle. In embodiments, the administration comprises using a 30 gauge needle. In some embodiments, the administration comprises using a ½ inch long 30 gauge needle.

The protocol of Table 6 can be adjusted based on treatment goals and results. For example, the number of injections to the upper frontalis at the hairline per side can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the upper frontalis can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the upper frontalis can be intramuscular injections as described in Table 5.

The dosage per injection site to the upper frontalis can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the upper frontalis can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

In the embodiments of Table 5, the number of injections to the corrugator per side (reference numeral 7 in FIG. 4) can be 1, 2, 3, 4, or the like, or between 1 and 4 injections, between 1 and 3 injections, between 2 and 4 injections, or the like. The injections to the corrugator can be parallel to the muscle. The injections to the corrugator can be to multiple total sites, for example, 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the corrugator can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the corrugator can be, for example, 3 units, 4 units, 5 units, 6 units, 7 units, 8 units, 9 units, 10 units, 11 units, 12 units, 13 units, 14 units, 15 units, 16 units, between 3 and 16 units, between 3 and 14 units, between 3 and 12 units, between 4 and 16 units, between 5 and 15 units, between 6 and 14 units, between 7 and 13 units, between 8 and 12 units, between 9 and 11 units, or the like.

In the embodiments of Table 5, the number of injections to the oculi (reference numeral 6 in FIG. 4) per side can be 1, 2, 3, 4, or the like, or between 1 and 4 injections, between 1 and 3 injections, between 2 and 4 injections, or the like. The injections to the oculi can be to multiple total sites, for example 2 sites, 3 sites, 4 sites, 5 sites, 6 sites, or 7 sites, or 8 sites, or the like, or to between 2 and 8 sites, between 2 and 6 sites, between 2 and 4 sites, between 3 and 6 sites, between 3 and 5 sites, or the like.

The dosage per injection site to the oculi can be, for example, 1 unit, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the oculi can be, for example, 2, 3 units, 4 units, 5 units, 6 units, 7 units, 8 units, 9 units, 10 units, 11 units, 12 units, 13 units, 14 units, 15 units, 16 units, 17, 18, 19, and 20, between 2 and 20 units, between 4 and 18 units, between 6 and 16 units, between 8 and 14 units, between 8 and 12 units, between 9 and 11 units, or the like.

In the embodiments of Table 6, the number of injections to the temporalis per side (reference numerals 3, 4, and 5 in FIG. 4) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the temporalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the temporalis can be, for example, 2 units, 3 units, 4 units, 5 units, 10 units, 15 units, 20 units, between 2 and 10 units, between 4 and 8 units, between 4 and 6 units, between 5 and 20 units, between 5 and 15 units, between 5 and 10 units, between 10 and 15 units, between 8 and 12 units, between 9 and 11 units, or the like.

The total dosage to the temporalis can be, for example, 15 units, 20 units, 25 units, 30 units, 35 units, 40 units, 45 units, 50 units, 55 units, 60 units, 65 units, 70 units, 75 units, 80 units, or the like, or between 20 and 80 units, between 25 and 75 units, between 30 and 70 units, between 35 and 65 units, between 50 and 70, between 55 and 65 units, or the like.

In the embodiments of Table 4, the number of IM injections per side to the nasalis (reference numeral 9 in FIG. 4) can be 1, 2, 3 or the like, or between 1 and 3 injections, or the like. The injections to the nasalis can be subcutaneous as described in Table 3 or superficial intramuscular as described in Table 4.

In the embodiments of Table 4, the total number of IM injections to the nasalis can be 1, 2, 3, 4, 5, 6, or the like, or between 1 and 6 injections, between 1 and 3 injections, between 2 and 4 injections, between 3 and 5, between 4 and 6, between 1 and 4, or the like.

The dosage per IM injection site to the nasalis can be, for example, 1 unit, 1.5 units 2 units, 2.5 units, 3 units, 3.5 units, 4 units, 4.5 units, 5 units, between 1 and 5 units, between 2 and 4 units, between 2 and 3 units, or the like.

The total IM dosage to the nasalis can be, for example, 2 units, 3 units, 4 units, 5 units, 6 units, 7 units, 8 units, 9 units, 10 units, between 2 and 10 units, between 3 and 9 units, between 4 and 8 units, between 4 and 6 units, between 5 and 10 units, between 5 and 8 units, or the like.

In the embodiments of Table 6, the number of injections (reference numeral 13 in FIG. 4) per side to the masseter can be 1, 2, 3, 4, or the like, or between 1 and 4 injections, between 1 and 3 injections, between 2 and 4 injections, or the like.

In the embodiments of Table 6, the total number of injections to the masseter can be 1, 2, 3, 4, 5, 6, 7, 8, or the like, or between 1 and 4 injections, between 1 and 3 injections, between 2 and 4 injections, between 4 and 6, between 4 and 8, or the like.

The dosage per injection site to the masseter can be, for example, 2 units, 3 units, 4 units, 5 units, 6 units, 7 units, 8 units, 9 units, 10 units, between 2 and 10 units, between 3 and 9 units, between 4 and 8 units, between 4 and 6 units, or the like.

The total dosage to the masseter can be, for example, 4 units, 5 units, 6 units, 7 units, 8 units, 9 units, 10 units, 11 units, 12 units, 13 units, 14 units, 15 units, 16 units, 17 units, 18 units, 19 units, 20 units, between 4 and 20 units, between 6 and 18 units, between 8 and 16 units, between 10 and 14 units, between 8 and 12 units, between 9 and 11 units, or the like.

In the embodiments of Table 6, the number of injections to the occipitalis per side (reference numerals 10, 11, and 12 in FIG. 4; mid-point of nuchal ridge for the first injection, which is done above the ridge. In embodiments the second and third injections form an inverted triangle with the first, and there is a about 2-3 cm between each injection point) can be 1, 2, 3, 4, 5, 6, 7, or the like, or between 1 and 6 injections, between 1 and 5 injections, between 2 and 6 injections, between 3 and 6 injections, between 2 and 5 injections, between 2 and 4 injections, or the like. The injections to the occipitalis can be to multiple total sites, for example 4 sites, 5 sites, 6 sites, 7 sites, 8 sites, 9 sites, or the like, or to between 2 and 8 sites, between 2 and 7 sites, between 3 and 6 sites, between 3 and 5 sites, between 5 and 7 sites, between 4 and 8 sites, or the like.

The dosage per injection site to the occipitalis can be, for example, 5 units, 10 units, 15 units, 20 units, between 5 and 20 units, between 5 and 15 units, between 5 and 10 units, between 10 and 15 units, or the like.

The total dosage to the occipitalis can be, for example, 20 units, 25 units, 30 units, 35 units, 40 units, 45 units, 50 units, 55 units, 60 units, 65 units, 70 units, 75 units, 80 units, 85 units, or between 20 and 40 units, between 25 and 35 units, 35 and 80 units, between 35 and 65 units, between 45 and 70 units, between 50 and 80 units, between 40 and 85 units, between 50 and 70 units, between 55 and 65 units, between 45 and 70 units, between 55 and 75 units, between 65 and 80 units, or the like.

In the embodiments of Table 6, the number of injection locations to the trapezius per side (superior [reference numeral 2 in FIG. 4] and inferior [reference numeral 1 in FIG. 4]) can be 1, 2, 3, 4, 5, or the like, or between 1 or 2 injections per side, between 1 and 3 injections, between 1 and 4 injections, between 1 and 5 injections, between 2 and 4 injections, between 2 and 5 injections, or the like. The injections to the trapezius (superior and inferior) can be to multiple sites, for example 2 sites, 3 sites, 4 sites, 5 sites, 6 sites, or 7 sites, or 8 sites, or the like, or to between 2 and 8 sites, between 2 and 7 sites, between 3 and 6 sites, between 3 and 5 sites, or the like. The injections to the superior trapezius can be subdermal as described on Table 3 or superficial intramuscular injections as described in Table 4. The injections to the inferior trapezius can be intramuscular as described in Table 3 and Table 4.

The dosage per injection site to the trapezius (superior and inferior) can be, for example, 2 units, 5 units, 10 units, 15 units, 20 units, between 5 and 20 units, between 5 and 15 units, between 5 and 10 units, between 10 and 15 units, between 15 and 20 units, between 4 and 6 units, between 2 and 8 units, between 8 and 12 units, or the like.

The total dosage to the trapezius (superior and inferior) can be, for example, 5 units, 10 units, 15 units, 20 units, 25 units, 30 units, 35 units, 40 units, 45 units, 50 units, 55 units, 60 units, or between 5 and 40 units, between 5 and 35 units, between 5 and 30 units, between 10 and 40 units, between 10 and 35 units, between 10 and 30 units, between 15 and 40 units, between 15 and 35 units, between 15 and 30 units, between 20 and 40 units, between 20 and 30 units, between 25 and 40 units, between 25 and 35 units, between 30 and 60 units, between 35 and 55 units, or the like.

In embodiments, methods comprise avoiding administering a therapeutically effective amount of at least one neurotoxin to a nerve associated with at least one of the nasalis, orbicularis oculi, frontalis, corrugator, procerus, occipitalis, temporalis, trapezius, masseter and cervical paraspinal muscle regions. For example, disclosed embodiments comprise administration to the nasalis and orbicularis oculi and corrugator and procerus and occipitalis and temporalis and trapezius and masseter, but not the cervical paraspinal muscle region or the frontalis. Other disclosed embodiments comprise administration to the orbicularis oculi and corrugator and procerus and occipitalis and temporalis and trapezius, but not the cervical paraspinal muscle region or the frontalis or nasalis or masseter. Similarly, disclosed embodiments comprise administration to the corrugator and procerus and occipitalis and temporalis and trapezius, but not the frontalis muscle region, or administration to the corrugator and procerus and occipitalis and temporalis and trapezius, but not the frontalis muscle region or cervical paraspinal region.

In embodiments, the cervical paraspinal is not administered-to.

In embodiments, the frontalis is not administered-to.

In embodiments, the corrugator is not administered-to.

In embodiments, the masseter is not administered-to.

In embodiments, the procerus is not administered-to.

In embodiments, the occipitalis is not administered-to.

In embodiments, the temporalis is not administered-to.

In embodiments, the trapezius is not administered-to.

In embodiments, the orbicularis oculi is not administered-to.

In embodiments, the nasalis is not administered-to.

Further embodiments comprise administering a therapeutically effective amount of at least one neurotoxin into the SPG. Such administration can comprise an injection, for example an intra-oral injection, an intra-nasal injection, or an injection through the cheek, in embodiments performed bi-laterally.

In embodiments, the amount injected into the SPG is half of the amount injected into at least one of the nasalis, orbicularis oculi, corrugator, procerus, occipitalis, temporalis, and trapezius muscle regions. In embodiments, the amount injected into the SPG is less than half of the amount injected into at least one of the nasalis, orbicularis oculi, corrugator, procerus, masseter, occipitalis, temporalis, and trapezius muscle regions. In embodiments, the amount injected into the SPG is more than half of the amount injected into at least one of the nasalis, orbicularis oculi, corrugator, procerus, occipitalis, temporalis, and trapezius muscle regions.

Disclosed methods can comprise use of multiple clostridial neurotoxins. For example, botulinum type A can be administered to the SPG, while botulinum type E can be administered to at least one of the nasalis, orbicularis oculi, corrugator, procerus, masseter occipitalis, temporalis, and trapezius muscle regions. In embodiments, botulinum type E can be administered to the SPG, while botulinum type A can be administered to at least one of the nasalis, orbicularis oculi, corrugator, procerus, masseter, occipitalis, temporalis, and trapezius muscle regions.

Neurotoxin Dosages

The neurotoxin can be administered in an amount of between about $10^{-3}$ U/kg and about 35 U/kg. In an embodiment, the neurotoxin is administered in an amount of between about $10^{-2}$ U/kg and about 25 U/kg. In another embodiment, the neurotoxin is administered in an amount of between about $10^{-1}$ U/kg and about 15 U/kg. In another embodiment, the neurotoxin is administered in an amount of between about 1 U/kg and about 10 U/kg. In many instances, an administration of from about 1 unit to about 300 Units of a neurotoxin, such as a botulinum type A, provides effective therapeutic relief. In an embodiment, from about 5 Units to about 200 Units of a neurotoxin, such as a botulinum type A, can be used and in another embodiment, from about 10 Units to about 100 Units of a neurotoxin, such as a botulinum type A, can be locally administered into a target tissue.

In embodiments, administration can comprise a total dose per treatment session of about 30 Units of a botulinum neurotoxin, or about 35 Units, or about 40 Units, or about 45 Units, or about 50 Units, or about 55 Units, or about 60 Units, or about 65 Units, or about 70 Units, or about 75 Units, or about 80 Units, or about 85 Units, or about 90 Units, or about 95 Units, or about 100 Units, or about 105 Units, or about 110 Units, or about 115 Units, or about 120 Units, or about 125 Units, or about 130 Units, or about 135 Units, or about 140 Units, or about 145 Units, or about 150 Units, or about 155 Units, or about 160 Units, or about 165 Units, or about 170 Units, or about 175 Units, or about 180 Units, or about 185 Units, or about 190 Units, or about 195 Units, or about 200 Units, or about 205 Units, or about 210 Units, or about 215 Units, or about 220 Units, or about 225 Units, or about 230 Units, or about 235 Units, or about 240 Units, or about 245 Units, or about 250 Units, or about 255 Units, or about 260 Units, or about 265 Units, or about 270 Units, or about 275 Units, or about 280 Units, or about 285 Units, or about 290 Units, or about 295 Units, or about 300 Units, or the like.

In embodiments, administration can comprise a total dose per treatment session of not less than 10 Units of a neurotoxin, for example botulinum type A neurotoxin, or not less than 15 Units, or not less than 20 Units, or not less than 25 Units, or not less than 30 Units, or not less than 35 Units, or not less than 40 Units, or not less than 45 Units, or not less than 50 Units, or not less than 55 Units, or not less than 60 Units, or not less than 65 Units, or not less than 70 Units, or not less than 75 Units, or not less than 80 Units, or not less than 85 Units, or not less than 90 Units, or not less than 95 Units, or not less than 100 Units, or not less than 105 Units, or not less than 110 Units, or not less than 115 Units, or not less than 120 Units, or not less than 125 Units, or not less than 130 Units, or not less than 135 Units, or not less than 140 Units, or not less than 145 Units, or not less than 150 Units, or not less than 155 Units, or not less than 160 Units, or not less than 165 Units, or not less than 170 Units, or not less than 175 Units, or not less than 180 Units, or not less than 185 Units, or not less than 190 Units, or not less than 195 Units, or not less than 200 Units, or not less than 205 Units, or not less than 210 Units, or not less than 215 Units, or not less than 220 Units, or not less than 225 Units, or not less than 230 Units, or not less than 235 Units, or not less than 240 Units, or not less than 245 Units, or not less than 250 Units, or not less than 255 Units, or not less than 260 Units, or not less than 265 Units, or not less than 270 Units, or not less than 275 Units, or not less than 280 Units, or not less than 285 Units, or not less than 290 Units, or not less than 295 Units, or not less than 300 Units, or the like.

In embodiments, administration can comprise a total dose per treatment session of not more than 10 Units of a neurotoxin, for example botulinum type A neurotoxin, or not more than 15 Units, or not more than 20 Units, or not more than 25 Units, or not more than 30 Units, or not more than 35 Units, or not more than 40 Units, or not more than 45 Units, or not more than 50 Units, or not more than 55 Units, or not more than 60 Units, or not more than 65 Units, or not more than 70 Units, or not more than 75 Units, or not more than 80 Units, or not more than 85 Units, or not more than 90 Units, or not more than 95 Units, or not more than 100 Units, or not more than 105 Units, or not more than 110 Units, or not more than 115 Units, or not more than 120 Units, or not more than 125 Units, or not more than 130 Units, or not more than 135 Units, or not more than 140 Units, or not more than 145 Units, or not more than 150 Units, or not more than 155 Units, or not more than 160 Units, or not more than 165 Units, or not more than 170 Units, or not more than 175 Units, or not more than 180 Units, or not more than 185 Units, or not more than 190 Units, or not more than 195 Units, or not more than 200 Units, or not more than 205 Units, or not more than 210 Units, or not more than 215 Units, or not more than 220 Units, or not more than 225 Units, or not more than 230 Units, or not more than 235 Units, or not more than 240 Units, or not more than 245 Units, or not more than 250 Units, or not more than 255 Units, or not more than 260 Units, or not more than 265 Units, or not more than 270 Units, or not more than 275 Units, or not more than 280 Units, or not more than 285 Units, or not more than 290 Units, or not more than 295 Units, or not more than 300 Units, or the like.

In embodiments, administration can comprise a total dose per year of not more than 400 Units of a neurotoxin, for example botulinum type A neurotoxin, or not more than 500 Units, or not more than 600 Units, or not more than 700 Units, or not more than 800 Units, or not more than 900 Units, or not more than 1000 Units, or the like.

In embodiments, neurotoxin administration, for example botulinum administration, to the nerve associated with at least one of the frontalis, corrugator, procerus, masseter occipitalis, temporalis, trapezius and cervical paraspinal muscle regions can comprise a total dose per treatment session of about 40 Units of a botulinum neurotoxin, or about 45 Units, or about 50 Units, or about 55 Units, or about 60 Units, or about 65 Units, or about 70 Units, or about 75 Units, or about 80 Units, or about 85 Units, or about 90 Units, or about 95 Units, or about 100 Units, or about 105 Units, or about 110 Units, or about 115 Units, or about 120 Units, or about 125 Units, or about 130 Units, or about 135 Units, or about 140 Units, or about 145 Units, or about 150 Units, or about 155 Units, or about 160 Units, or about 165 Units, or about 170 Units, or about 175 Units, or about 180 Units, or about 185 Units, or about 190 Units, or about 195 Units, or about 200 Units, or about 205 Units, or about 210 Units, or the like.

In embodiments, neurotoxin administration, for example botulinum administration, to the SPG, can comprise a total dose per treatment session of about 5 Units of a botulinum neurotoxin, or about 10 Units, or about 15 Units, or about 20 Units, or about 25 Units, or about 30 Units, or about 35 Units, or about 40 Units, or about 45 Units, or about 50 Units, or about 55 Units, or about 60 Units, or about 65 Units, or about 70 Units, or about 75 Units, or about 80 Units, or about 85 Units, or about 90 Units, or about 95 Units, or about 100 Units, or about 105 Units, or about 110 Units, or about 115 Units, or about 120 Units, or about 125 Units, or about 130 Units, or about 135 Units, or about 140 Units, or about 145 Units, or the like.

In embodiments, the dose of the neurotoxin is expressed in protein amount or concentration. For example, in embodiments the neurotoxin can be administered in an amount of between about 0.2 ng and 20 ng. In an embodiment, the neurotoxin is administered in an amount of between about 0.3 ng and 19 ng, about 0.4 ng and 18 ng, about 0.5 ng and 17 ng, about 0.6 ng and 16 ng, about 0.7 ng and 15 ng, about 0.8 ng and 14 ng, about 0.9 ng and 13 ng, about 1.0 ng and 12 ng, about 1.5 ng and 11 ng, about 2 ng and 10 ng, about 5 ng and 7 ng, and the like, into a target tissue such as a muscle.

Ultimately, however, both the quantity of toxin administered and the frequency of its administration will be at the discretion of the physician responsible for the treatment and will be commensurate with questions of safety and the effects produced by the toxin.

Disclosed embodiments comprise treatments that can be repeated. For example, a repeat treatment can be performed when the patient begins to experience CM symptoms. However, preferred embodiments comprise repeating the treatment prior to the return of symptoms. Therefore, disclosed embodiments comprise repeating the treatment, for example, after 4 weeks, after 5 weeks, after 6 weeks, 8 weeks, 10 weeks, 12 weeks, 14 weeks, 16 weeks, 18 weeks, 20 weeks, 22 weeks, 24 weeks, or more. Repeat treatments can comprise administration sites that differ from the administration sites used in a prior treatment. For example, in embodiments, the frontalis can be injected in the initial treatment, then not injected in a following treatment.

A controlled release system can be used in the embodiments described herein to deliver a neurotoxin in vivo at a predetermined rate over a specific time period. A controlled release system can be comprised of a neurotoxin incorporated into a carrier. The carrier can be a polymer or a bio-ceramic material. The controlled release system can be injected, inserted or implanted into a selected location of a patient's body and reside therein for a prolonged period during which the neurotoxin is released by the implant in a manner and at a concentration which provides a desired therapeutic efficacy.

Polymeric materials can release neurotoxins due to diffusion, chemical reaction or solvent activation, as well as upon influence by magnetic, ultrasound or temperature change factors. Diffusion can be from a reservoir or matrix. Chemical control can be due to polymer degradation or cleavage of the drug from the polymer. Solvent activation can involve swelling of the polymer or an osmotic effect.

A kit for practicing disclosed embodiments is also encompassed by the present disclosure. The kit can comprise a 33 gauge or smaller needle and a corresponding syringe. The kit can also comprise at least one Clostridial neurotoxin composition, such as a botulinum type A toxin composition. The neurotoxin composition may be provided in the syringe. The composition is injectable through the needle. The kits are designed in various forms based the sizes of the syringe and the needles and the volume of the injectable composition(s) contained therein, which in turn are based on the specific deficiencies the kits are designed to treat.

EXAMPLES

The following non-limiting Examples are provided for illustrative purposes only in order to facilitate a more complete understanding of representative embodiments. This example should not be construed to limit any of the embodiments described in the present specification.

Example 1

Treatment of Chronic Migraine

A chronic migraine patient is treated via injection of 15 U of botulinum type A each at several locations along the trigeminal nerve, including the frontalis, corrugator, procerus, and occipitalis. After an evaluation period of 12 weeks, the patient is also administered 30 U of botulinum type A (15 U bilaterally) intra-orally to the SPG.

The patient reports fewer migraines for 18 weeks following the treatment.

Example 2

Treatment of Chronic Migraine

A chronic migraine patient is treated via injection of 20 U of botulinum type A each at several locations along the trigeminal nerve, including the frontalis, corrugator, temporalis, and occipitalis. The patient is also administered 25 U of botulinum type A (12.5 U bilaterally) through the cheek to the SPG.

The patient reports fewer migraines for 16 weeks following the treatment.

Example 3

Treatment of Chronic Migraine

A chronic migraine patient is treated via injection of 25 U of botulinum type A each at several locations along the trigeminal nerve, including the corrugator, procerus, masseter, temporalis, trapezius, and occipitalis. The frontalis and the cervical paraspinal are not injected. The patient is also administered 30 U of botulinum type A (15 U bilaterally) through the cheek to the SPG.

The patient reports fewer migraines following the treatment, as well as a decrease in migraine symptoms when a migraine does occur. After a 12 week evaluation period, the injections into the SPG are repeated.

Example 4

Treatment of Chronic Migraine

A chronic migraine patient is treated via injection of 20 U of botulinum type A each at several locations along the trigeminal nerve, including the frontalis, procerus, and occipitalis. The corrugator is not injected. The patient is also administered 30 U of botulinum type A (15 U bilaterally) through the cheek to the SPG.

The patient reports fewer migraine symptoms for 18 weeks following the treatment.

Example 5

Treatment of Chronic Migraine

A chronic migraine patient is treated via injection of 15 U of botulinum type A each at several locations along the trigeminal nerve, including the frontalis, corrugator, procerus, and occipitalis. The cervical paraspinal region is not injected. The patient is also administered 30 U of botulinum type A (15 U bilaterally) intra-orally to the pterygopalatine space.

Example 6

Treatment of Episodic Migraine

An episodic migraine patient is treated via injection of 15 U of botulinum type A each at several locations along the trigeminal nerve, including the frontalis, corrugator, procerus, masseter, and occipitalis. The cervical paraspinal region is not injected. The patient is also administered 30 U of botulinum type A (15 U bilaterally) intra-orally to the pterygopalatine space.

The patient reports fewer migraines for 16 weeks following the treatment.

Example 7

Treatment of Chronic Migraine

A chronic migraine patient is treated via injection of 25 U of botulinum type A each at several locations along the trigeminal nerve, including the corrugator, procerus, masseter, temporalis, trapezius, and occipitalis (as shown in FIG. 1). The frontalis and cervical paraspinal regions are not injected. The patient is also administered 30 U of botulinum type A (15 U bilaterally) intra-orally to the pterygopalatine space.

The patient reports fewer migraines for 16 weeks following the treatment.

Example 8

Treatment of Chronic Migraine

A chronic migraine patient is treated via injection of 30 U of botulinum type A each at several locations along the trigeminal nerve, including the corrugator, procerus, masseter, temporalis, trapezius, and occipitalis (as shown in FIG. 1). The frontalis and cervical paraspinal regions are not injected.

The patient reports fewer migraines for 12 weeks following the treatment.

Example 9

Treatment of Chronic Migraine

A chronic migraine patient is treated via injection of 15 U of botulinum type A each at several locations along the trigeminal nerve, including the corrugator, procerus, and occipitalis. The frontalis is not injected, to reduce the risk of the patient developing ptosis.

After an evaluation period of 12 weeks, the patient is also administered 30 U of botulinum type A (15 U bilaterally) intra-orally to the SPG.

The patient reports fewer migraines for 18 weeks following the treatment. No ptosis is reported.

Example 10

Treatment of Chronic Migraine

A chronic migraine patient is treated via injection of 20 U of botulinum type A each at several locations along the trigeminal nerve, including the corrugator, temporalis, and occipitalis. The frontalis is not injected, to reduce the risk of the patient developing ptosis. The patient is also administered 25 U of botulinum type A (12.5 U bilaterally) through the cheek to the SPG.

The patient reports fewer migraines for 16 weeks following the treatment. No ptosis is reported.

Example 11

Treatment of Chronic Migraine

A chronic migraine patient is treated via injection of 25 U of botulinum type A each at several locations along the trigeminal nerve, including the corrugator, procerus, masseter, temporalis, trapezius, and occipitalis. The frontalis and the cervical paraspinal are not injected, to reduce the risk of the patient developing ptosis or neck muscle weakness. The patient is also administered 30 U of botulinum type A (15 U bilaterally) through the cheek to the SPG.

The patient reports fewer migraines following the treatment, as well as a decrease in migraine symptoms when a migraine does occur. After a 12 week evaluation period, the injections into the SPG are repeated. No ptosis or neck muscle weakness is reported.

Example 12

Treatment of Chronic Migraine

A chronic migraine patient is treated via injection of 20 U of botulinum type A each at several locations along the trigeminal nerve, including the frontalis, procerus, and occipitalis. The cervical paraspinal muscles are not injected, to reduce the risk of the patient developing neck weakness. The patient is also administered 30 U of botulinum type A (15 U bilaterally) through the cheek to the SPG.

The patient reports fewer migraine symptoms for 18 weeks following the treatment. No neck weakness is reported.

Example 13

Treatment of Chronic Migraine

A chronic migraine patient is treated via injection of 15 U of botulinum type A each at several locations along the trigeminal nerve, including the corrugator, procerus, and occipitalis. The cervical paraspinal region is not injected, to reduce the risk of the patient developing neck weakness. The patient is also administered 20 U of botulinum type A (10 U bilaterally) intra-orally to the pterygopalatine space. No neck weakness is reported.

Example 14

Treatment of Episodic Migraine

An episodic migraine patient is treated via injection of 25 U of botulinum type A each at several locations along the trigeminal nerve, including the corrugator, procerus, masseter, and occipitalis. The cervical paraspinal region is not injected, to reduce the risk of the patient developing neck weakness. The patient is also administered 30 U of botulinum type A (15 U bilaterally) intra-orally to the pterygopalatine space.

The patient reports fewer migraines for 14 weeks following the treatment. No neck weakness is reported.

Example 15

Treatment of Chronic Migraine

A chronic migraine patient is treated via injection of 25 U of botulinum type A each at several locations along the trigeminal nerve, including the corrugator, procerus, masseter, temporalis, trapezius, and occipitalis. The frontalis and cervical paraspinal regions are not injected, to reduce the risk of the patient developing ptosis or neck muscle weakness.

The patient reports fewer migraines for 18 weeks following the treatment. No neck weakness or ptosis is reported.

Example 16

Treatment of Chronic Migraine

A chronic migraine patient is treated via injection of 30 U of botulinum type A each at several locations along the trigeminal nerve, including the nasalis, procerus, masseter, temporalis, trapezius, corrugator, and occipitalis. The frontalis and cervical paraspinal regions are not injected, to reduce the risk of the patient developing ptosis or neck muscle weakness.

The patient reports fewer migraines for 12 weeks following the treatment. No ptosis or neck weakness is reported.

Example 17

Treatment of Chronic Migraine

A chronic migraine patient is treated via injection of 30 U of botulinum type A each at several locations along the trigeminal nerve, including the nasalis, orbicularis oculi, procerus, masseter, temporalis, trapezius, corrugator, and occipitalis. The frontalis and cervical paraspinal regions are not injected, to reduce the risk of the patient developing ptosis or neck muscle weakness.

The patient reports fewer migraines for 12 weeks following the treatment. No ptosis or neck weakness is reported.

Example 18

Treatment of Chronic Migraine

A chronic migraine patient is treated via injection of 30 U of botulinum type A each at several locations along the trigeminal nerve, including the orbicularis oculi, procerus, masseter, temporalis, trapezius, corrugator, and occipitalis. The frontalis and cervical paraspinal regions are not injected, to reduce the risk of the patient developing ptosis or neck muscle weakness.

The patient reports fewer migraines for 12 weeks following the treatment. No ptosis or neck weakness is reported.

Example 19

Treatment of Migraine

A migraine patient with EM is treated via the following injection protocol: the trapezius is injected with 5 units botulinum type A per injection at two sites (superior) and 10 units per injection at two sites (inferior) on each side of the head as described in Table 1. The occipitalis is injected with 10 units per site at three sites on each side of the head, while the temporalis is injected with 5 units per site at three sites anterior to the tragus on each side of the head.

The procerus is injected at one site with 5 units. The corrugator is injected with 5 units per site at two sites, one on each side of the head. The oculi is injected with 5 units per site at two sites, one on each side of the head.

The patient reports fewer migraines for 12 weeks following the treatment.

Example 20

Treatment of Migraine

A migraine patient with EM is treated via the following injection protocol: the trapezius is injected with 4 units botulinum type A per injection at two sites (superior) and 10 units per injection at two sites (inferior) on each side of the head as described in Table 1. The occipitalis is injected with 11 units per site at three sites on each side of the head, while the temporalis is injected with 4 units per site at three sites anterior to the tragus on each side of the head.

The procerus is injected at one site with 6 units. The corrugator is injected with 7 units per site at two sites, one on each side of the head. The oculi is injected with 4 units per site at two sites, one on each side of the head.

The patient reports fewer migraines for 12 weeks following the treatment.

Example 21

Treatment of Migraine

A migraine patient with EM is treated via the following injection protocol: the trapezius is injected with 5 units botulinum type B per injection at two sites (superior) and 11 units per injection at two sites (inferior) on each side of the head as described in Table 1. The occipitalis is injected with 9 units per site at three sites on each side of the head, while the temporalis is injected with 4 units per site at three sites anterior to the tragus on each side of the head.

The procerus is injected at one site with 10 units. The corrugator is injected with 4 units per site at two sites, one on each side of the head. The oculi is injected with 7 units per site at two sites, one on each side of the head.

The patient reports fewer migraines for 16 weeks following the treatment.

Example 22

Treatment of Migraine

A migraine patient with EM is treated via the following injection protocol: the trapezius is injected with 6 units botulinum type A per injection at two sites (superior) and 10 units per injection at two sites (inferior) on each side of the head as described in Table 1. The occipitalis is injected with 10 units per site at three sites on each side of the head, while the temporalis is injected with 5 units per site at three sites anterior to the tragus on each side of the head.

The procerus is injected at one site with 11 units. The corrugator is injected with 4 units per site at two sites, one on each side of the head. The oculi is injected with 6 units per site at two sites, one on each side of the head.

The patient reports fewer migraines for 16 weeks following the treatment.

Example 23

Treatment of Migraine

A migraine patient with EM is treated via the following injection protocol: the trapezius is injected with 5 units botulinum type A per injection at two sites (superior) and 10 units per injection at two sites (inferior) on each side of the head as described in Table 2 and the following paragraphs. The occipitalis is injected with 10 units per site at three sites on each side of the head, while the temporalis is injected with 5 units per site at three sites anterior to the tragus on each side of the head.

The procerus is injected at one site with 5 units. The corrugator is injected with 5 units per site at two sites, one on each side of the head. The oculi is injected with 5 units per site at two sites, one on each side of the head.

The patient reports fewer migraines for 16 weeks following the treatment.

Example 24

Treatment of Migraine

A migraine patient with EM is treated via the following injection protocol: the trapezius is injected with 5 units botulinum type A per injection at two sites (superior) and 10 units per injection at two sites (inferior) on each side of the head as described in Table 2 and the following paragraphs. The occipitalis is injected with 9 units per site at three sites on each side of the head, while the temporalis is injected with 5 units per site at three sites anterior to the tragus on each side of the head.

The procerus is injected at one site with 6 units. The corrugator is injected with 6 units per site at two sites, one on each side of the head. The oculi is injected with 4 units per site at two sites, one on each side of the head.

The patient reports fewer migraines for 13 weeks following the treatment.

Example 25

Treatment of Migraine

A migraine patient with EM is treated via the following injection protocol: the trapezius is injected with 6 units botulinum type A per injection at two sites (superior) and 10 units per injection at two sites (inferior) on each side of the head as described in Table 2 and the following paragraphs. The occipitalis is injected with 11 units per site at three sites on each side of the head, while the temporalis is injected with 6 units per site at three sites anterior to the tragus on each side of the head.

The procerus is injected at one site with 7 units. The corrugator is injected with 5 units per site at two sites, one on each side of the head. The oculi is injected with 8 units per site at two sites, one on each side of the head.

The patient reports fewer migraines for 18 weeks following the treatment.

Example 26

Treatment of Migraine

A migraine patient with EM is treated via the following injection protocol: the trapezius is injected with 6 units botulinum type A per injection at two sites (superior) and 9 units per injection at two sites (inferior) on each side of the head as described in Table 2 and the following paragraphs. The occipitalis is injected with 10 units per site at three sites on each side of the head, while the temporalis is injected with 6 units per site at three sites anterior to the tragus on each side of the head.

The procerus is injected at one site with 4 units. The corrugator is injected with 6 units per site at two sites, one on each side of the head. The oculi is injected with 5 units per site at two sites, one on each side of the head.

The patient reports fewer migraines for 12 weeks following the treatment.

Example 27

Treatment of Migraine

A migraine patient with EM is treated via the following injection protocol: the trapezius is injected with botulinum type A per injection at two sites (5 units superior and 10 units inferior for a total of 10 units superior and 20 units inferior) on each side of the head as described in Table 3 and the following paragraphs. The occipitalis is injected with 10 units per site at three sites on each side of the head, while the temporalis is injected with 10 units per site at three sites anterior to the tragus on each side of the head.

The procerus is injected at one site with 8 units. The corrugator is injected with 6 units per site at two sites, one on each side of the head. The oculi is injected with 5 units per site at two sites, one on each side of the head.

The patient reports fewer migraines for 14 weeks following the treatment.

Example 28

Treatment of Migraine

A migraine patient with CM is treated via the following injection protocol: the trapezius is injected with botulinum type B per injection at two sites (6 units superior and 9 units inferior for a total of 12 units superior and 18 units inferior) on each side of the head as described in Table 3 and the following paragraphs. The occipitalis is injected with 9 units per site at three sites on each side of the head, while the temporalis is injected with 10 units per site at three sites anterior to the tragus on each side of the head.

The procerus is injected at one site with 5 units. The corrugator is injected with 5 units per site at two sites, one on each side of the head. The oculi is injected with 6 units per site at two sites, one on each side of the head.

The patient reports fewer migraines for 10 weeks following the treatment.

Example 29

Treatment of Migraine

A migraine patient with CM is treated via the following injection protocol: the trapezius is injected with botulinum type A per injection at two sites (4 units superior and 11 units inferior for a total of 8 units superior and 22 units inferior) on each side of the head as described in Table 3 and the following paragraphs. The occipitalis is injected with 10 units per site at three sites on each side of the head, while the temporalis is injected with 10 units per site at three sites anterior to the tragus on each side of the head.

The procerus is injected at one site with 7 units. The corrugator is injected with 6 units per site at two sites, one on each side of the head. The oculi is injected with 5 units per site at two sites, one on each side of the head.

The patient reports fewer migraines for 14 weeks following the treatment.

Example 30

Treatment of Migraine

A migraine patient with CM is treated via the following injection protocol: the trapezius is injected with botulinum type A per injection at two sites (5 units superior and 10 units inferior for a total of 10 units superior and 20 units inferior) on each side of the head as described in Table 3 and the following paragraphs. The occipitalis is injected with 10 units per site at three sites on each side of the head, while the temporalis is injected with 10 units per site at three sites anterior to the tragus on each side of the head.

The procerus is injected at one site with 6 units. The corrugator is injected with 6 units per site at two sites, one on each side of the head. The oculi is injected with 5 units per site at two sites, one on each side of the head.

The nasalis is injected 2.5 units at one site on each side of the head, and the masseter is injected with 5 units at one site on each side of the head.

The patient reports fewer migraines for 12 weeks following the treatment.

Example 31

Treatment of Migraine

A migraine patient with CM is treated via the following injection protocol: the trapezius is injected with botulinum type A per injection at two sites (5 units superior and 10 units inferior for a total of 10 units superior and 20 units inferior) on each side of the head as described in Table 4 and the following paragraphs. The occipitalis is injected with 10 units per site at three sites on each side of the head, while the temporalis is injected with 10 units per site at three sites anterior to the tragus on each side of the head.

The procerus is injected at one site with 5 units. The corrugator is injected with 5 units per site at two sites, one on each side of the head. The oculi is injected with 5 units per site at two sites, one on each side of the head.

The nasalis is injected 2.5 units at one site on each side of the head, and the masseter is injected with 5 units at one site on each side of the head.

The patient reports fewer migraines for 17 weeks following the treatment.

Example 32

Treatment of Migraine

A migraine patient with CM is treated via the following injection protocol: the trapezius is injected with botulinum type A per injection at two sites (4 units superior and 11 units inferior for a total of 8 units superior and 22 units inferior) on each side of the head as described in Table 4 and the following paragraphs. The occipitalis is injected with 9 units per site at three sites on each side of the head, while the temporalis is injected with 10 units per site at three sites anterior to the tragus on each side of the head.

The procerus is injected at one site with 6 units. The corrugator is injected with 5 units per site at two sites, one on each side of the head. The oculi is injected with 5 units per site at two sites, one on each side of the head.

The nasalis is injected 3 units at one site on each side of the head, and the masseter is injected with 4 units at one site on each side of the head.

The patient reports fewer migraines for 12 weeks following the treatment.

Example 33

Treatment of Migraine

A migraine patient is treated via the following injection protocol: the trapezius is injected with botulinum type A per injection at two sites (5 units superior and 10 units inferior for a total of 10 units superior and 20 units inferior) on each side of the head as described in Table 4 and the following paragraphs. The occipitalis is injected with 11 units per site at three sites on each side of the head, while the temporalis is injected with 10 units per site at three sites anterior to the tragus on each side of the head.

The procerus is injected at one site with 4 units. The corrugator is injected with 6 units per site at two sites, one on each side of the head. The oculi is injected with 5 units per site at two sites, one on each side of the head.

The nasalis is injected 2.5 units at one site on each side of the head, and the masseter is injected with 5 units at one site on each side of the head.

The patient reports fewer migraines for 18 weeks following the treatment.

Example 34

Treatment of Migraine

A migraine patient is treated via the following injection protocol: the trapezius is injected with botulinum type E per injection at two sites (5 units superior and 10 units inferior for a total of 10 units superior and 20 units inferior) on each side of the head as described in Table 4 and the following paragraphs. The occipitalis is injected with 9 units per site at three sites on each side of the head, while the temporalis is injected with 10 units per site at three sites anterior to the tragus on each side of the head.

The procerus is injected at one site with 6 units. The corrugator is injected with 6 units per site at two sites, one on each side of the head. The oculi is injected with 5 units per site at two sites, one on each side of the head.

The nasalis is injected 2.5 units at one site on each side of the head, and the masseter is injected with 5 units at one site on each side of the head.

The patient reports fewer migraines for 12 weeks following the treatment.

Example 35

Treatment of Migraine

A migraine patient is treated with botulinum type A via the following injection protocol: the frontalis is injected at or near the hairline with a 5 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear threading approach injections, one 5 unit IM injection in each side of the medial corrugator muscle. The needle is inserted at the medial edge of the corrugator muscle (at the vertical crease line) and parallel to the orbital ridge horizontal plane (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 5 units per site at two sites, one on each side of the head made at a 45-degree angle to the face with only the bevel inserted.

The temporalis is injected with 5 units per site at three sites anterior to the tragus on each side of the head by injecting the most anterior of the three sites at the hairline and angling the needle back towards the hairline of the temporal area to avoid the antra-temporal fasci.

The occipitalis is injected with 10 units per site at three sites on each side of the head, by inserting the needle parallel to the nuchal ridge. The plunger is depressed as the needle is withdrawn towards the injection site (parallel linear threading approach). The injection is directed laterally for first half of the dose and medially for the second half of the dose. The "linear threading" approach should allow for diffusion into the occipitalis area and greater and lesser occipital nerves The trapezius is injected at two sites (5 units superior and 10 units inferior for a total of 10 units superior and 20 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear threading approach). For the inferior trapezius, the injection is made at a 45-degree angle at the top of the slope of the trapezius. The "linear threading" approach allows for diffusion into the superior trapezius area and $3^{rd}$ occipital nerve Example 36

Treatment of Migraine

A migraine patient is treated with botulinum type A via the following injection protocol: the frontalis is injected at or near the hairline with a 6 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear threading approach injections, one 6 unit IM injection in each side of the medial corrugator muscle. The needle is inserted at the medial edge of the corrugator muscle (at the vertical crease line) and parallel to the orbital ridge horizontal plane (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 4 units per site at two sites, one on each side of the head made at a 45-degree angle to the face with only the bevel inserted.

The temporalis is injected with 7 units per site at three sites anterior to the tragus on each side of the head by injecting the most anterior of the three sites at the hairline and angling the needle back towards the hairline of the temporal area to avoid the antra-temporal fasci.

The occipitalis is injected with 9 units per site at three sites on each side of the head, by inserting the needle parallel to the nuchal ridge. The plunger is depressed as the needle is withdrawn towards the injection site (parallel linear threading approach). The injection is directed laterally for first half of the dose and medially for the second half of the dose. The "linear threading" approach should allow for diffusion into the occipitalis area and greater and lesser occipital nerves The trapezius is injected at two sites (6 units superior and 9 units inferior for a total of 12 units superior and 18 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear threading approach). For the inferior trapezius, the injection is made at a 45-degree angle at the top of the slope of the trapezius. The "linear threading" approach allows for diffusion into the superior trapezius area and $3^{rd}$ occipital nerve Example 37

Treatment of Migraine

A migraine patient is treated with botulinum type B via the following injection protocol: the frontalis is injected at the hairline with a 5 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear thread approach injections, one 5 unit IM injection in each side of medial corrugator muscle. The needle is inserted at the medial edge of the corrugator muscle (at the vertical crease line) and parallel to the orbital ridge horizontal plain (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 5 units per site at two sites, one on each side of the head made at a 45-degree angle to the face with only the bevel inserted.

The temporalis is injected with 8 units per site at three sites anterior to the tragus on each side of the head by injecting at the hairline and angling the needle back towards the hairline of the temporal area to avoid the antra-temporal fasci.

The occipitalis is injected with 10 units per site at three sites on each side of the head, by inserting the needle parallel to the nuchal ridge. The plunger is depressed as the needle is withdrawn towards the injection site (parallel linear thread approach). The injection is directed laterally for first half of the dose and medially for the second half of the dose. The "linear threading" approach should allow for diffusion into the occipitalis area and greater and lesser occipital nerves The trapezius is injected at two sites (6 units superior and 9 units inferior for a total of 12 units superior and 18 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear thread approach). For the inferior trapezius, the injection is made at a 45-degree angle at the top of the slope of the trapezius. The "linear threading" approach allows for diffusion into the superior trapezius area and 3rd occipital nerve Example 38

Treatment of Migraine

A migraine patient is treated with botulinum type E via the following injection protocol: the frontalis is injected at the hairline with a 7 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear thread approach injections, one 7 unit IM injection in each side of medial corrugator muscle. The needle is inserted at the medial edge of the corrugator muscle (at the vertical crease line) and parallel to the orbital ridge horizontal plain (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 4 units per site at two sites, one on each side of the head made at a 45-degree angle to the face with only the bevel inserted.

The temporalis is injected with 8 units per site at three sites anterior to the tragus on each side of the head by injecting at the hairline and angling the needle back towards the hairline of the temporal area to avoid the antra-temporal fasci.

The occipitalis is injected with 10 units per site at three sites on each side of the head, by inserting the needle parallel to the nuchal ridge. The plunger is depressed as the needle is withdrawn towards the injection site (parallel linear thread approach). The injection is directed laterally for first half of the dose and medially for the second half of the dose. The "linear threading" approach should allow for diffusion into the occipitalis area and greater and lesser occipital nerves The trapezius is injected at two sites (5 units superior and 10 units inferior for a total of 10 units superior and 20 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear thread approach). For the inferior trapezius, the injection is made at a 45-degree angle at the top of the slope of the trapezius. The "linear threading" approach allows for diffusion into the superior trapezius area and 3rd occipital nerve

Example 39

Treatment of Migraine

A migraine patient is treated with botulinum type B via the following injection protocol: the frontalis is injected at the hairline with a 7 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear thread approach injections, one 5 unit IM injection in each side of medial corrugator muscle. The needle is inserted at the medial edge of the corrugator muscle (at the vertical crease line) and parallel to the orbital ridge horizontal plain (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 5 units per site at two sites, one on each side of the head made at a 45-degree angle to the face with only the bevel inserted.

The temporalis is injected with 8 units per site at three sites anterior to the tragus on each side of the head by injecting at the hairline and angling the needle back towards the hairline of the temporal area to avoid the antra-temporal fasci.

The occipitalis is injected with 8 units per site at three sites on each side of the head, by inserting the needle parallel to the nuchal ridge. The plunger is depressed as the needle is withdrawn towards the injection site (parallel linear thread approach). The injection is directed laterally for first half of the dose and medially for the second half of the dose. The "linear threading" approach should allow for diffusion into the occipitalis area and greater and lesser occipital nerves The trapezius is injected at two sites (6 units superior and 9 units inferior for a total of 12 units superior and 18 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear thread approach). For the inferior trapezius, the injection is made at a 45-degree angle at the top of the slope of the trapezius. The "linear threading" approach allows for diffusion into the superior trapezius area and $3^{rd}$ occipital nerve

Example 40

Treatment of Migraine

A migraine patient is treated with botulinum type A via the following injection protocol: the frontalis is injected at or near the hairline with a 5 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear threading approach injections, one 5 unit IM injection in each side of the medial corrugator muscle. The needle is inserted at the medial edge of the corrugator muscle (at the vertical crease line) and parallel to the orbital ridge horizontal plane (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 5 units per site at two sites, one on each side of the head made at a 45-degree angle to the face with only the bevel inserted.

The temporalis is injected with 10 units per site at three sites anterior to the tragus on each side of the head by injecting the most anterior of the three sites at the hairline and angling the needle back towards the hairline of the temporal area to avoid the antra-temporal fasci.

The occipitalis is injected with 10 units per site at three sites on each side of the head, by inserting the needle parallel to the nuchal ridge. The plunger is depressed as the needle is withdrawn towards the injection site (parallel linear threading approach). The injection is directed laterally for first half of the dose and medially for the second half of the dose. The "linear threading" approach should allow for diffusion into the occipitalis area and greater and lesser occipital nerves The trapezius is injected at two sites (5 units superior and 10 units inferior for a total of 10 units superior and 20 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear threading approach). For the inferior trapezius, the injection is made at a 45-degree angle at the top of the slope of the trapezius. The "linear threading" approach allows for diffusion into the superior trapezius area and $3^{rd}$ occipital nerve The nasalis is injected with 2.5 units at one site on each side of the head.

The masseter is injected with 5 units at one site on each side of the head.

Example 41

Treatment of Migraine

A migraine patient is treated with botulinum type A via the following injection protocol: the frontalis is injected at or near the hairline with a 6 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear threading approach injections, one 6 unit IM injection in each side of the medial corrugator muscle. The needle is inserted at the medial edge of the corrugator muscle (at the vertical crease line) and parallel to the orbital ridge horizontal plane (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 4 units per site at two sites, one on each side of the head made at a 45-degree angle to the face with only the bevel inserted.

The temporalis is injected with 7 units per site at three sites anterior to the tragus on each side of the head by injecting the most anterior of the three sites at the hairline and angling the needle back towards the hairline of the temporal area to avoid the antra-temporal fasci.

The occipitalis is injected with 9 units per site at three sites on each side of the head, by inserting the needle parallel to the nuchal ridge. The plunger is depressed as the needle is withdrawn towards the injection site (parallel linear threading approach). The injection is directed laterally for first half of the dose and medially for the second half of the dose. The "linear threading" approach should allow for diffusion into the occipitalis area and greater and lesser occipital nerves The trapezius is injected at two sites (6 units superior and 9 units inferior for a total of 12 units superior and 18 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear threading approach). For the inferior trapezius, the injection is made at a 45-degree angle at the top of the slope of the trapezius. The "linear threading" approach allows for diffusion into the superior trapezius area and $3^{rd}$ occipital nerve.

The nasalis is injected with 3 units at one site on each side of the head.

The masseter is injected with 4 units at one site on each side of the head.

Example 42

Treatment of Migraine

A migraine patient is treated with botulinum type B via the following injection protocol: the frontalis is injected at the hairline with a 5 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear thread approach injections, one 5 unit IM injection in each side of medial corrugator muscle. The needle is inserted at the medial edge of the corrugator muscle (at the vertical crease line) and parallel to the orbital ridge horizontal plain (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 5 units per site at two sites, one on each side of the head made at a 45-degree angle to the face with only the bevel inserted.

The temporalis is injected with 8 units per site at three sites anterior to the tragus on each side of the head by injecting at the hairline and angling the needle back towards the hairline of the temporal area to avoid the antra-temporal fasci.

The occipitalis is injected with 10 units per site at three sites on each side of the head, by inserting the needle parallel to the nuchal ridge. The plunger is depressed as the needle is withdrawn towards the injection site (parallel linear thread approach). The injection is directed laterally for first half of the dose and medially for the second half of the dose. The "linear threading" approach should allow for diffusion into the occipitalis area and greater and lesser occipital nerves The trapezius is injected at two sites (6 units superior and 9 units inferior for a total of 12 units superior and 18 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear thread approach). For the inferior trapezius, the injection is made at a 45-degree angle at the top of the slope of the trapezius. The "linear threading" approach allows for diffusion into the superior trapezius area and $3^{rd}$ occipital nerve.

The nasalis is injected with 2.5 units at one site on each side of the head.

The masseter is injected with 6 units at one site on each side of the head.

Example 43

Treatment of Migraine

A migraine patient is treated with botulinum type E via the following injection protocol: the frontalis is injected at the hairline with a 7 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear thread approach injections, one 7 unit IM injection in each side of medial corrugator muscle. The needle is inserted at the medial edge of the corrugator muscle (at the vertical crease line) and parallel to the orbital ridge horizontal plain (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 4 units per site at two sites, one on each side of the head made at a 45-degree angle to the face with only the bevel inserted.

The temporalis is injected with 8 units per site at three sites anterior to the tragus on each side of the head by injecting at the hairline and angling the needle back towards the hairline of the temporal area to avoid the antra-temporal fasci.

The occipitalis is injected with 10 units per site at three sites on each side of the head, by inserting the needle parallel to the nuchal ridge. The plunger is depressed as the needle is withdrawn towards the injection site (parallel linear thread approach). The injection is directed laterally for first half of the dose and medially for the second half of the dose. The "linear threading" approach should allow for diffusion into the occipitalis area and greater and lesser occipital nerves The trapezius is injected at two sites (5 units superior and 10 units inferior for a total of 10 units superior and 20 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear thread approach). For the inferior trapezius, the injection is made at a 45-degree angle at the top of the slope of the trapezius. The "linear threading" approach allows for diffusion into the superior trapezius area and 3rd occipital nerve.

The nasalis is injected with 3.5 units at one site on each side of the head.

The masseter is injected with 5 units at one site on each side of the head.

Example 44

Treatment of Migraine

A migraine patient is treated with botulinum type B via the following injection protocol: the frontalis is injected at the hairline with a 7 unit injection on each side of the head, with a lateral injection starting at the limbic line where the forehead starts to angle backwards, injecting at a 45-degree angle, angling away from the lower forehead.

The corrugator is then injected near the medial line, utilizing 2 parallel linear thread approach injections, one 5 unit IM injection in each side of medial corrugator muscle. The needle is inserted at the medial edge of the corrugator muscle (at the vertical crease line) and parallel to the orbital ridge horizontal plain (parallel to the muscle above the eyebrow) and perpendicular to the corrugator skin line. The skin is slightly angled to skin coming in on the medial edge and the needle is injected ½" while holding the muscle. The plunger is depressed as the needle is withdrawn towards the injection site and stopped at the medial line.

The oculi is injected with 5 units per site at two sites, one on each side of the head made at a 45-degree angle to the face with only the bevel inserted.

The temporalis is injected with 8 units per site at three sites anterior to the tragus on each side of the head by injecting at the hairline and angling the needle back towards the hairline of the temporal area to avoid the antra-temporal fasci.

The occipitalis is injected with 8 units per site at three sites on each side of the head, by inserting the needle parallel to the nuchal ridge. The plunger is depressed as the needle is withdrawn towards the injection site (parallel linear thread approach). The injection is directed laterally for first half of the dose and medially for the second half of the dose. The "linear threading" approach should allow for diffusion into the occipitalis area and greater and lesser occipital nerves.

The trapezius is injected at two sites (6 units superior and 9 units inferior for a total of 12 units superior and 18 units inferior) on each side of the head as described in Table 5 and the following paragraphs. The patient is injected at a 45-degree angle away from the mid-neck for the superior trapezius injection and parallel to C2. The plunger is depressed as the needle is withdrawn towards the injection site (parallel linear thread approach). For the inferior trapezius, the injection is made at a 45-degree angle at the top of the slope of the trapezius. The "linear threading" approach allows for diffusion into the superior trapezius area and 3rd occipital nerve.

In embodiments, the nasalis is injected with 2 units at one site on each side of the head.

In embodiments, the masseter is injected with 6 units at one site on each side of the head.

Example 45

Treatment of Migraine

A migraine patient is treated with botulinum type A in accordance with the injection protocols of Table 5 or Table 6, using the following syringe allocation for each of the injection sites specified in Table 5 or Table 6:
   a. Frontal injections comprise the following:
      i. Syringe 1-32G: injections 1 & 2 to the oculi for a total of 2 injections;
      ii. Syringe 2-32G: injections 1 & 2 to the corrugator, injections 3 and 4 to the frontalis for a total of 4 injections;
      iii. Syringe 3-32G: injections 1 & 2 to the nasalis for a total of 2 injections;
      iv. Syringe 4-30G: injections 1 and 2 to the masseter for a total of 2 injections;
      v. Syringe 5-32G: injections 1-3 to the right side of the temporalis for a total of 3 injections;
      vi. Syringe 6-32G: injections 1-3 to the left side of the temporalis for a total of 3 injections;
   b. Posterior injections comprise the following:
      i. Syringe 7-32G: injections 1-3 to the right side of the occipitalis (since fanning) for a total of 3 injections;
      ii. Syringe 8-32G: injections 1-3 to the left side of the occipitalis (since fanning) for a total of 3 injections;
      iii. Syringe 9-32G: injections 1 & 2 to the superior trapezius, injections 3 & 4 to the inferior trapezius, for a total of 4 injections.

Example 46

Treatment of Migraine

A migraine patient is treated with botulinum type A in accordance with the injection protocols of Table 5 or Table 6, using the following syringe allocation for each of the injection sites specified in Table 5 or Table 6:
   a. Frontal injections comprise the following:
      i. Syringe 1-32G: injections 1 & 2 to the oculi for a total of 2 injections;
      ii. Syringe 2-32G: injections 1 & 2 to the corrugator, injections 3 and 4 to the frontalis for a total of 4 injections;
      iii. Syringe 3-32G: injections 1 & 2 to the nasalis, injections 3 and 4 to the masseter for a total of 4 injections;
      iv. Syringe 5-32G: injections 1-3 to the right side of the temporalis for a total of 3 injections;
      v. Syringe 6-32G: injections 1-3 to the left side of the temporalis for a total of 3 injections;
   b. Posterior injections comprise the following:
      i. Syringe 7-32G: injections 1-3 to the right side of the occipitalis (since fanning) for a total of 3 injections;
      ii. Syringe 8-32G: injections 1-3 to the left side of the occipitalis (since fanning) for a total of 3 injections;
      iii. Syringe 9-32G: injections 1 & 2 to the superior trapezius, injections 3 & 4 to the inferior trapezius, for a total of 4 injections.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The following embodiments are specifically contemplated:

Embodiment 1) A method for reducing the severity of a symptom associated with Episodic (EM) or Chronic Migraine (CM) comprising:
  a. administering a first clostridial neurotoxin into at least one of the frontalis, corrugator, procerus, masseter, occipitalis, temporalis, trapezius and cervical paraspinal muscle regions;
  b. administering a second clostridial neurotoxin bilaterally into the Sphenopalatine Ganglion (SPG);
  c. thereby reducing the severity of the symptom associated with EM or CM.

Embodiment 2) The method of embodiment 1, wherein said administering comprises injection of the first and second clostridial neurotoxins.

Embodiment 3) The method of embodiment 2, wherein said first and second clostridial neurotoxins comprise botulinum neurotoxins.

Embodiment 4) The method of embodiment 3, wherein said botulinum neurotoxins comprise botulinum type A.

Embodiment 5) The method of embodiment 1, wherein the total dose of the first clostridial neurotoxin is 50-100 Units.

Embodiment 6) The method of embodiment 1, wherein the total dose of the second clostridial neurotoxin is 25-50 Units.

Embodiment 7) The method of embodiment 6, wherein the second clostridial toxin is injected intra-orally, through the cheek, or nasally.

Embodiment 8) The method of embodiment 4, wherein said clostridial neurotoxins comprise native botulinum type A.

Embodiment 9) The method of embodiment 3, wherein said botulinum neurotoxins comprise botulinum type B.

Embodiment 10) The method of embodiment 1, wherein said first clostridial neurotoxin is administered in an amount at least twice that of said second clostridial neurotoxin.

Embodiment 11) The method of embodiment 1, wherein said administering a first clostridial neurotoxin comprises injection into the corrugator.

Embodiment 12) The method of embodiment 1, wherein said administering a first clostridial neurotoxin comprises injection into the procerus.

Embodiment 13) The method of embodiment 1, wherein said administering a first clostridial neurotoxin comprises injection into the occipitalis.

Embodiment 14) The method of embodiment 1, wherein said administering a first clostridial neurotoxin comprises injection into the temporalis.

Embodiment 15) The method of embodiment 1, wherein said administering a first clostridial neurotoxin comprises injection into the trapezius.

Embodiment 16) The method of any of embodiments 11-15 wherein said clostridial neurotoxins comprise a botulinum type A neurotoxin.

Embodiment 17) A method for comparing the efficacy and safety of two different clostridial toxins, comprising:
  a. measuring a reduction of a migraine symptom of an individual resulting from administration of a first botulinum neurotoxin;
  b. measuring a side effect in an individual resulting from administration of a first botulinum neurotoxin;
  c. measuring a reduction of a migraine symptom of an individual resulting from administration of a second clostridial neurotoxin;
  d. measuring a side effect in an individual resulting from administration of a first botulinum neurotoxin; and
  e. comparing the reduction in symptoms and the reduction in side effects to determine a difference between the first botulinum neurotoxin and the second botulinum neurotoxin.

Embodiment 18) A method for reducing the severity of a symptom associated with an episodic (EM) or Chronic Migraine (CM) comprising:
  a. administering a first clostridial neurotoxin into at least one of the frontalis, corrugator, procerus, occipitalis, temporalis, trapezius, masseter and cervical paraspinal muscle regions;
  b. evaluating the effect of the first clostridial neurotoxin after 12 weeks has elapsed, then if further treatment is necessary administering a second clostridial neurotoxin bilaterally into the Sphenopalatine Ganglion (SPG);
  c. thereby reducing the severity of the symptom associated with EM or CM.

Embodiment 19) The method of embodiment 18, wherein said administering comprises injection of the first and second clostridial neurotoxins.

Embodiment 20) The method of embodiment 19, wherein said first and second clostridial neurotoxins comprise botulinum neurotoxins.

Embodiment 21) The method of embodiment 20, wherein said botulinum neurotoxins comprise botulinum type A.

Embodiment 22) The method of embodiment 18, wherein the total dose of the first clostridial neurotoxin is 50-100 Units.

Embodiment 23) The method of embodiment 18, wherein the total dose of the second clostridial neurotoxin is 25-50 Units.

Embodiment 24) The method of embodiment 21, wherein second botulinum toxin is injected intra-orally, through the cheek, or nasally.

Embodiment 25) The method of embodiments 1, 17, or 18, wherein said clostridial toxin is botulinum type A.

Embodiment 26) The method of embodiments 1, 17, or 18, wherein said clostridial toxin is botulinum type B.

Embodiment 27) The method of embodiments 1, 17, or 18, wherein said clostridial toxin is botulinum type C.

Embodiment 28) The method of embodiments 1, 17, or 18, wherein said clostridial toxin is botulinum type E.

Embodiment 29) The method of embodiment 1, 17, or 18, wherein said clostridial toxin is botulinum type F.

Embodiment 30) A method for reducing the severity of a symptom associated with an episodic (EM) or Chronic Migraine (CM) comprising:
  a. administering a first clostridial neurotoxin into at least one of the corrugator, procerus, masseter, occipitalis, temporalis, trapezius, nasalis, and orbicularis oculi muscle regions, wherein at least one of the frontalis and cervical paraspinal muscles are not treated;

b. thereby reducing the severity of the symptom associated with EM or CM.

Embodiment 31) The method of embodiment 30, wherein said administering comprises injection of the first and second clostridial neurotoxins.

Embodiment 32) The method of embodiment 31, wherein said first and second clostridial neurotoxins comprise botulinum neurotoxins.

Embodiment 33) The method of embodiment 32, wherein said botulinum neurotoxins comprise botulinum type A.

Embodiment 34) The method of embodiment 30, wherein the total dose of the first clostridial neurotoxin is 50-100 Units.

Embodiment 35) The method of embodiment 30, wherein the total dose of the second clostridial neurotoxin is 25-50 Units.

Embodiment 36) The method of embodiment 35, wherein second clostridial toxin is injected intra-orally, through the cheek, or nasally.

Embodiment 37) The method of embodiment 33, wherein said botulinum neurotoxins comprise native botulinum type A.

Embodiment 38) The method of embodiment 35, wherein said clostridial neurotoxins comprise botulinum type B.

Embodiment 39) The method of embodiment 30, wherein said first clostridial neurotoxin is administered in an amount at least twice that of said second clostridial neurotoxin.

Embodiment 40) The method of embodiment 30, wherein said administering a first clostridial neurotoxin comprises injection into the corrugator.

Embodiment 41) The method of embodiment 30, wherein said administering a first clostridial neurotoxin comprises injection into the procerus.

Embodiment 42) The method of embodiment 30, wherein said administering a first clostridial neurotoxin comprises injection into the occipitalis.

Embodiment 43) The method of embodiment 30, wherein said administering a first clostridial neurotoxin comprises injection into the temporalis.

Embodiment 44) The method of embodiment 30, wherein said administering a first clostridial neurotoxin comprises injection into the trapezius.

Embodiment 45) The method of embodiment 30, wherein the frontalis is not treated.

Embodiment 46) The method of embodiment 30, wherein the cervical paraspinals are not treated.

Embodiment 47) A method for reducing the side effects of treating a symptom associated with an episodic (EM) or Chronic Migraine (CM) comprising:

a. administering a first clostridial neurotoxin into at least one of the corrugator, procerus, occipitalis, temporalis, trapezius, nasalis, masseter, and orbicularis oculi muscle regions, wherein at least one of the frontalis and cervical paraspinal muscles are not treated;

b. thereby reducing the side effects of treating a symptom associated with EM or CM.

Embodiment 48) The method of embodiment 47, wherein said administering comprises injection of the first and second clostridial neurotoxins.

Embodiment 49) The method of embodiment 48, wherein said first and second clostridial neurotoxins comprise botulinum neurotoxins.

Embodiment 50) The method of embodiment 49, wherein said botulinum neurotoxins comprise botulinum type A.

Embodiment 51) The method of embodiment 47, wherein the total dose of the first clostridial neurotoxin is 50-100 Units.

Embodiment 52) The method of embodiment 47, wherein the total dose of the second clostridial neurotoxin is 25-50 Units.

Embodiment 53) The method of embodiment 52, wherein second clostridial toxin is injected intra-orally, through the cheek, or nasally.

Embodiment 54) The method of embodiments 30 or 47, wherein said clostridial toxin is botulinum type B.

Embodiment 55) The method of embodiments 30 or 47, wherein said clostridial toxin is botulinum type C.

Embodiment 56) The method of embodiments 30 or 47, wherein said clostridial toxin is botulinum type E.

Embodiment 57) The method of embodiments 30 or 47, wherein said clostridial toxin is botulinum type F.

Embodiment 58) The method of embodiment 30, further comprising administering a second clostridial neurotoxin bilaterally into the Sphenopalatine Ganglion (SPG).

Embodiment 59) The method of embodiment 47, further comprising administering evaluating the effect of the original administration and if necessary administrating a second clostridial neurotoxin bilaterally into the Sphenopalatine Ganglion (SPG).

Embodiment 60) A method for reducing the severity of a symptom associated with Episodic Migraine (EM) comprising:

a. administering a clostridial toxin to the superior trapezius at a dosage of about 5 units on each side of the head and about 10 units to the inferior trapezius on each side of the head;

b. administering a clostridial toxin to the occipitalis at a dosage of about 10 units at three sites on each side of the head;

c. administering a clostridial toxin to the temporalis at a dosage of about 5 units at three sites on each side of the head;

d. administering a clostridial toxin to the procerus at a dosage of about 5 units to one site;

e. administering a clostridial toxin to the corrugator at a dosage of about 5 units to one site on each side of the head;

f. administering a clostridial toxin to the oculi at a dosage of about 5 units on each side of the head;

g. thereby reducing the severity of the symptom associated with EM.

Embodiment 61) The method of embodiment 60, wherein said clostridial toxin is selected from the group consisting of botulinum type B, botulinum type C, botulinum type E, and botulinum type F.

Embodiment 62) The method of embodiment 60, wherein said clostridial toxin is botulinum type A.

Embodiment 63) The method of embodiment 60, wherein said clostridial toxin is administered subdermally to the superior trapezius and by intramuscular injection to the inferior trapezius, occipitalis, temporalis, procerus, corrugator and oculi.

Embodiment 64) The method of embodiment 60, wherein said clostridial toxin is administered by superficial intramuscular injection to the superior trapezius and by intramuscular injection to the inferior trapezius, occipitalis, temporalis, procerus, corrugator and oculi.

Embodiment 65) The method of embodiment 60, wherein said clostridial toxin is administered by intramuscular injection to the superior trapezius, inferior trapezius, occipitalis, temporalis, procerus, corrugator and oculi.

Embodiment 66) A method for reducing the severity of a symptom associated with Episodic Migraine (EM) comprising:
   a. administering a clostridial toxin to the superior trapezius at a dosage of about 3-10 units on each side of the head and about 5-15 units to the inferior trapezius on each side of the head;
   b. administering a clostridial toxin to the occipitalis at a dosage of about 5-15 units at three sites on each side of the head;
   c. administering a clostridial toxin to the temporalis at a dosage of about 3-10 units at three sites on each side of the head;
   d. administering a clostridial toxin to the procerus at a dosage of about 3-10 units to one site;
   e. administering a clostridial toxin to the corrugator at a dosage of about 3-10 units to one site on each side of the head;
   f. administering a clostridial toxin to the oculi at a dosage of about 3-10 units on each side of the head;
   g. thereby reducing the severity of the symptom associated with EM.

Embodiment 67) The method of embodiment 66, wherein said clostridial toxin is selected from the group consisting of botulinum type B, botulinum type C, botulinum type E, and botulinum type F.

Embodiment 68) The method of embodiment 66, wherein said clostridial toxin is botulinum type A.

Embodiment 69) The method of embodiment 66, wherein said clostridial toxin is administered subdermally to the superior trapezius and by intramuscular injection to the inferior trapezius, occipitalis, temporalis, procerus, corrugator and oculi.

Embodiment 70) The method of embodiment 66, wherein said clostridial toxin is administered by superficial intramuscular injection to the superior trapezius and by intramuscular injection to the inferior trapezius, occipitalis, temporalis, procerus, corrugator and oculi.

Embodiment 71) The method of embodiment 66, wherein said clostridial toxin is administered by intramuscular injection to the superior trapezius, inferior trapezius, occipitalis, temporalis, procerus, corrugator and oculi.

Embodiment 72) A method for reducing the severity of a symptom associated with Chronic Migraine (CM) comprising:
   a. administering a clostridial toxin to the superior trapezius at a dosage of about 5 units on each side of the head and about 10 units to the inferior trapezius on each side of the head;
   b. administering a clostridial toxin to the occipitalis at a dosage of about 10 units at three sites on each side of the head;
   c. administering a clostridial toxin to the temporalis at a dosage of about 10 units at three sites on each side of the head;
   d. administering a clostridial toxin to the procerus at a dosage of about 5 units to one site;
   e. administering a clostridial toxin to the corrugator at a dosage of about 5 units to one site a clostridial toxin to the oculi at a dosage of about 5 units on each side of the head;
   f. administering a clostridial toxin to the nasalis at a dosage of about 2.5 units on each side of the head;
   g. administering a clostridial toxin to the masseter at a dosage of 5 units on each side of the head;
   h. thereby reducing the severity of the symptom associated with CM.

Embodiment 73) The method of embodiment 72, wherein said clostridial toxin is selected from the group consisting of botulinum type B, botulinum type C, botulinum type E, and botulinum type F.

Embodiment 74) The method of embodiment 72, wherein said clostridial toxin is botulinum type A.

Embodiment 75) The method of embodiment 72, wherein said clostridial toxin is administered subdermally to the superior trapezius, by subcutaneous injection to the nasalis, and by intramuscular injection to the inferior trapezius, occipitalis, temporalis, procerus, corrugator, oculi and masseter.

Embodiment 76) The method of embodiment 72, wherein said clostridial toxin is administered by superficial intramuscular injection to the superior trapezius and the nasalis, and by intramuscular injection to the inferior trapezius, occipitalis, temporalis, procerus, corrugator, oculi, and masseter.

Embodiment 77) The method of embodiment 72, wherein said clostridial toxin is administered by intramuscular injection to the superior trapezius, inferior trapezius, occipitalis, temporalis, procerus, corrugator, oculi, nasalis and masseter.

Embodiment 78) The method of embodiment 72, wherein said clostridial toxin is administered to the temporalis anterior to the tragus.

Embodiment 79) A method for reducing the severity of a symptom associated with Chronic Migraine (CM) comprising:
   a. administering a clostridial toxin to the superior trapezius at a dosage of about 3-10 units on each side of the head and 5-15 units to the inferior trapezius on each side of the head;
   b. administering a clostridial toxin to the occipitalis at a dosage of about 5-15 units at three sites on each side of the head;
   c. administering a clostridial toxin to the temporalis at a dosage of about 5-15 units at three sites on each side of the head;
   d. administering a clostridial toxin to the procerus at a dosage of about 3-10 units to one site;
   e. administering a clostridial toxin to the corrugator at a dosage of about 3-10 units to one site on each side of the head;
   f. administering a clostridial toxin to the oculi at a dosage of about 3-10 units on each side of the head;
   g. administering a clostridial toxin to the nasalis at a dosage of about 2-4 units on each side of the head;
   h. administering a clostridial toxin to the masseter at a dosage of about 3-10 units on each side of the head;
   i. thereby reducing the severity of the symptom associated with CM.

Embodiment 80) The method of embodiment 79, wherein said clostridial toxin is selected from the group consisting of botulinum type B, botulinum type C, botulinum type E, and botulinum type F.

Embodiment 81) The method of embodiment 79, wherein said clostridial toxin is botulinum type A.

Embodiment 82) The method of embodiment 79, wherein said clostridial toxin is administered subdermally to the superior trapezius, by subcutaneous injection to the nasalis, and by intramuscular injection to the inferior trapezius, occipitalis, temporalis, procerus, corrugator, oculi and masseter.

Embodiment 83) The method of embodiment 79, wherein said clostridial toxin is administered by superficial intramuscular injection to the superior trapezius and the nasalis, and by intramuscular injection to the inferior trapezius, occipitalis, temporalis, procerus, corrugator, oculi, and masseter.

Embodiment 84) The method of embodiment 79, wherein said clostridial toxin is administered by intramuscular injection to the superior trapezius, inferior trapezius, occipitalis, temporalis, procerus, corrugator, oculi, nasalis and masseter.

Embodiment 85) The method of embodiment 79, wherein said clostridial toxin is administered to the temporalis anterior to the tragus.

Embodiment 86. The method of any of embodiments 60-71, further comprising at least one placebo injection.

Embodiment 87. The method of embodiment 84, wherein said placebo injection comprises at least one injection to the nasalis.

Embodiment 88. The method of embodiment 84, wherein said placebo injection comprises at least one injection to the masseter.

Embodiment 89) A method for reducing the severity of a symptom associated with migraine comprising:
 a. administering a clostridial toxin to the superior trapezius at a dosage of about 3-10 units per site at two sites on each side of the head and 5-15 units per site to the inferior trapezius at two sites on each side of the head;
 b. administering a clostridial toxin to the occipitalis at a dosage of about 7-15 units per site at three sites on each side of the head;
 c. administering a clostridial toxin to the temporalis at a dosage of about 3-15 units per site at three sites on each side of the head;
 d. administering a clostridial toxin to the oculi at a dosage of about 3-10 units to one site on each side of the head;
 e. administering a clostridial toxin to the corrugator at a dosage of about 3-10 units to one site on each side of the head;
 f. administering a clostridial toxin to the frontalis at a dosage of about 3-10 units to one site on each side of the head;
 g. thereby reducing the severity of the symptom associated with migraine.

Embodiment 90) The method of embodiment 89, wherein said clostridial toxin is selected from the group consisting of botulinum type B, botulinum type C, botulinum type E, and botulinum type F.

Embodiment 91) The method of embodiment 90, wherein said clostridial toxin is botulinum type A.

Embodiment 92) A method for reducing the severity of a symptom associated with migraine comprising:
 a. administering a clostridial toxin to the superior trapezius at a dosage of about 5 units per site at two sites on each side of the head and 10 units per site to the inferior trapezius at two sites on each side of the head;
 b. administering a clostridial toxin to the occipitalis at a dosage of about 10 units per site at three sites on each side of the head;
 c. administering a clostridial toxin to the temporalis at a dosage of about 5 units per site at three sites on each side of the head;
 d. administering a clostridial toxin to the oculi at a dosage of about 5 units to one site on each side of the head;
 e. administering a clostridial toxin to the corrugator at a dosage of about 5 units to one site on each side of the head;
 f. administering a clostridial toxin to the frontalis at a dosage of about 5 units to one site on each side of the head;
 g. thereby reducing the severity of the symptom associated with migraine.

Embodiment 93) The method of embodiment 92, wherein said clostridial toxin is selected from the group consisting of botulinum type B, botulinum type C, botulinum type E, and botulinum type F.

Embodiment 94) The method of embodiment 93, wherein said clostridial toxin is botulinum type A.

Embodiment 95) A method for reducing the severity of a symptom associated with Chronic Migraine (CM) comprising:
 a. administering a clostridial toxin to the superior trapezius at a dosage of about 3-10 units per site at two sites on each side of the head and 5-15 units per site to the inferior trapezius at two sites on each side of the head;
 b. administering a clostridial toxin to the occipitalis at a dosage of about 7-15 units per site at three sites on each side of the head;
 c. administering a clostridial toxin to the temporalis at a dosage of about 3-15 units per site at three sites on each side of the head;
 d. administering a clostridial toxin to the oculi at a dosage of about 3-10 units to one site on each side of the head;
 e. administering a clostridial toxin to the corrugator at a dosage of about 3-10 units to one site on each side of the head;
 f. administering a clostridial toxin to the frontalis at a dosage of about 3-10 units to one site on each side of the head;
 g. administering a clostridial toxin to the nasalis at a dosage of about 1-5 units to one site on each side of the head;
 h. administering a clostridial toxin to the masseter at a dosage of about 3-10 units to one site on each side of the head
 i. thereby reducing the severity of the symptom associated with CM.

Embodiment 96) The method of embodiment 95, wherein said clostridial toxin is selected from the group consisting of botulinum type B, botulinum type C, botulinum type E, and botulinum type F.

Embodiment 97) The method of embodiment 96, wherein said clostridial toxin is botulinum type A.

Embodiment 98) A method for reducing the severity of a symptom associated with Chronic Migraine (CM) comprising:
 a. administering a clostridial toxin to the superior trapezius at a dosage of about 5 units per site at two sites on each side of the head and 10 units per site to the inferior trapezius at two sites on each side of the head;
 b. administering a clostridial toxin to the occipitalis at a dosage of about 10 units per site at three sites on each side of the head;
 c. administering a clostridial toxin to the temporalis at a dosage of about 10 units per site at three sites on each side of the head;
 d. administering a clostridial toxin to the oculi at a dosage of about 5 units to one site on each side of the head;
 e. administering a clostridial toxin to the corrugator at a dosage of about 5 units to one site on each side of the head;
 f. administering a clostridial toxin to the frontalis at a dosage of about 5 units to one site on each side of the head;
 g. administering a clostridial toxin to the nasalis at a dosage of about 2.5 units to one site on each side of the head;

h. administering a clostridial toxin to the masseter at a dosage of about 5 units to one site on each side of the head i. thereby reducing the severity of the symptom associated with CM.

Embodiment 93) The method of embodiment 92, wherein said clostridial toxin is selected from the group consisting of botulinum type B, botulinum type C, botulinum type E, and botulinum type F.

Embodiment 94) The method of embodiment 92, wherein said clostridial toxin is botulinum type A.

Embodiment 95) The method of any of the preceding embodiments, wherein administration comprises use of a 32 gauge needle.

Embodiment 96) The method of embodiment 95, wherein said 32 gauge needle is ½" long.

Embodiment 97) The method of any of the preceding embodiments, wherein administration comprises use of a 31 gauge needle.

Embodiment 98) The method of embodiment 97, wherein said 31 gauge needle is ½" long.

Embodiment 99) The method of any of the preceding embodiments, wherein administration comprises use of a 29 gauge needle.

Embodiment 100) The method of embodiment 99, wherein said 29 gauge needle is ½" long.

Embodiment 101) The method of any of the preceding embodiments, wherein administration comprises use of a 28 gauge needle.

Embodiment 102) The method of embodiment 101, wherein said 28 gauge needle is ½" long.

Embodiment 103) The method of any of the preceding embodiments, wherein administration comprises use of a 27 gauge needle.

Embodiment 104) The method of embodiment 103, wherein said 27 gauge needle is ½" long.

The invention claimed is:

1. A method for treating a migraine headache comprising:
a) administering about 10 units of a botulinum neurotoxin into the upper frontalis at the hairline, and further administering the neurotoxin to at least five of the muscle regions selected from the corrugator, masseter, nasalis, oculi, occipitalis, temporalis, and trapezius muscle regions, and wherein the cervical paraspinal muscle and procerus muscles are not administered-to;
b) thereby treating the migraine headache.

2. The method of claim 1, wherein a second botulinum neurotoxin is administered bilaterally into the sphenopalatine ganglion (SPG).

3. The method of claim 1, wherein said botulinum neurotoxin is further administered to between five six and seven eight of the muscle regions selected from the corrugator, masseter, nasalis, occipitalis, temporalis, trapezius and oculi muscle regions.

4. The method of claim 1, wherein said botulinum neurotoxin is further administered to the corrugator, occipitalis, temporalis, and trapezius muscle regions.

5. The method of claim 1, wherein said botulinum neurotoxin is further administered to the corrugator, occipitalis, temporalis, oculi and trapezius muscle regions.

6. The method of claim 1, wherein said botulinum neurotoxin is further administered to the corrugator, occipitalis, temporalis, masseter and trapezius muscle regions.

7. The method of claim 1, wherein said botulinum neurotoxin is further administered to the corrugator, occipitalis, temporalis, oculi, nasalis, and trapezius muscle regions.

8. The method of claim 1, wherein said botulinum neurotoxin is further administered to the corrugator, occipitalis, temporalis, oculi, nasalis, masseter and trapezius muscle regions.

9. The method of claim 1, wherein said migraine headache is an episodic migraine or a chronic migraine.

10. The method of claim 9, wherein said migraine headache is an episodic migraine.

11. The method of claim 9, wherein said migraine headache is a chronic migraine.

12. The method of claim 1, wherein said botulinum neurotoxin comprises botulinum type A.

13. The method of claim 1, wherein said botulinum neurotoxin comprises botulinum type B, C, D, E, or F.

14. The method of claim 1, wherein the total dose of said botulinum neurotoxin is about 145-200 Units.

15. The method of claim 1, wherein the total dose of said botulinum neurotoxin is about 195 Units.

16. The method of claim 1, wherein the total dose of said botulinum neurotoxin is about 150 Units.

17. The method of claim 1, wherein said administration to said corrugator comprises administration of said botulinum neurotoxin in an amount of about 10 Units.

18. The method of claim 1, wherein said administration to said oculi comprises administration of said botulinum neurotoxin in an amount of about 10 Units.

19. The method of claim 1, wherein said administration to said temporalis comprises administration of said botulinum neurotoxin in an amount of about 30 Units anterior to the tragus.

20. The method of claim 1, wherein said administration to said temporalis comprises administration of said botulinum neurotoxin in an amount of about 60 Units anterior to the tragus.

21. The method of claim 1, wherein said administration to said nasalis comprises administration of said botulinum neurotoxin in an amount of about 5 Units.

22. The method of claim 1, wherein said administration to said masseter comprises administration of said botulinum neurotoxin in an amount of about 10 Units.

23. The method of claim 1, wherein said administration to said occipitalis comprises administration of said botulinum neurotoxin in an amount of about 60 Units.

24. The method of claim 1, wherein said administration to said trapezius comprises administration of said botulinum neurotoxin in an amount of about 30 Units.

25. The method of claim 24, wherein said administration to said trapezius comprises superficial administration of said botulinum neurotoxin in an amount of about 10 Units to the superior trapezius.

26. The method of claim 1, wherein said nasalis is not administered-to.

27. The method of claim 1, wherein said masseter is not administered-to.

28. A fixed-site, fixed-dose method for treating migraine with 22 individual botulinum administrations comprising:
administering a botulinum toxin to the superior trapezius at a dosage of about 5 units per site at one site on each side of the head and about 10 units per site to the inferior trapezius at one site on each side of the head; and
administering a botulinum toxin to the occipitalis at a dosage of about 10 units per site at three sites on each side of the head; and
administering a botulinum toxin to the temporalis at a dosage of about 5 units per site at three sites on each side of the head; and administering a botulinum toxin to the oculi at a dosage of about 5 units to one site on each side of the head; and administering a botulinum toxin to the corrugator at a dosage of about 5 units to one site on each side of the head; and administering a botulinum toxin to the upper frontalis at the hairline at a dosage of about 5 units to one site on each side of the head;

wherein the botulinum toxin is not administered to the cervical paraspinal or procerus muscles;

thereby treating the migraine with a total of about 150 Units.

29. A fixed-site, fixed-dose method for treating migraine with 26 individual botulinum administrations comprising:

administering a botulinum toxin to the superior trapezius at a dosage of about 5 units per site at one site on each side of the head and about 10 units per site to the inferior trapezius at one site on each side of the head; and administering a botulinum toxin to the occipitalis at a dosage of about 10 units per site at three sites on each side of the head; and administering a botulinum toxin to the temporalis at a dosage of about 10 units per site at three sites on each side of the head; and administering a botulinum toxin to the oculi at a dosage of about 5 units to one site on each side of the head; and administering a botulinum toxin to the corrugator at a dosage of about 5 units to one site on each side of the head; and administering a botulinum toxin to the upper frontalis at the hairline at a dosage of about 5 units to one site on each side of the head; and administering a botulinum toxin to the nasalis at a dosage of about 2.5 units to one site on each side of the head; and administering a botulinum toxin to the masseter at a dosage of about 5 units to one site on each side of the head;

wherein the botulinum toxin is not administered to the cervical paraspinal or procerus muscles;

thereby treating the migraine with a total of about 195 Units.

30. A fixed site method for treating migraine headache with 24 individual botulinum administrations comprising:

administering a botulinum toxin to the superior trapezius at a dosage of about 3-10 units per site at one site on each side of the head and 5-15 units per site to the inferior trapezius at one site on each side of the head; and administering a botulinum toxin to the occipitalis at a dosage of about 7-15 units per site at three sites on each side of the head; and administering a botulinum toxin to the temporalis at a dosage of about 3-15 units per site at three sites on each side of the head; and administering a botulinum toxin to the oculi at a dosage of about 3-10 units to one site on each side of the head; and administering a botulinum toxin to the corrugator at a dosage of about 3-10 units to one site on each side of the head; and administering a botulinum toxin to the upper frontalis at the hairline at a dosage of about 3-10 units to one site on each side of the head; and administering a botulinum toxin to at least one of the nasalis and masseter, wherein said nasalis administration is at a dosage of about 1-5 units to one site on each side of the head; and said masseter administration is at a dosage of about 3-10 units to one site on each side of the head;

wherein the botulinum toxin is not administered to the cervical paraspinal or procerus muscles;

thereby treating the migraine headache.

* * * * *